(12) United States Patent
Kimoto et al.

(10) Patent No.: US 7,962,098 B2
(45) Date of Patent: Jun. 14, 2011

(54) ANTENNA UNIT AND RECEIVING APPARATUS USING THE SAME

(75) Inventors: Seiichiro Kimoto, Hachioji (JP); Akira Matsui, Hino (JP)

(73) Assignee: Olympus Corporation, Tokyo (JP)

( * ) Notice: Subject to any disclaimer, the term of this patent is extended or adjusted under 35 U.S.C. 154(b) by 892 days.

(21) Appl. No.: 11/658,432

(22) PCT Filed: Sep. 7, 2005

(86) PCT No.: PCT/JP2005/016421
§ 371 (c)(1),
(2), (4) Date: Jan. 26, 2007

(87) PCT Pub. No.: WO2006/028134
PCT Pub. Date: Mar. 16, 2006

(65) Prior Publication Data
US 2009/0012360 A1    Jan. 8, 2009

(30) Foreign Application Priority Data

Sep. 7, 2004  (JP) .................................. 2004-260247
Sep. 8, 2004  (JP) .................................. 2004-261670
Sep. 8, 2004  (JP) .................................. 2004-261671

(51) Int. Cl.
*H04B 7/00* (2006.01)
(52) U.S. Cl. .................. 455/41.2; 455/41.3; 455/67.11; 340/539.12; 340/572.1; 600/300; 600/118
(58) Field of Classification Search .................. 455/41.2, 455/41.3, 67.11, 503, 515, 574, 127.5, 343.1, 455/343.5; 340/573.1, 539.12, 572.1; 600/300, 600/118
See application file for complete search history.

(56) References Cited

U.S. PATENT DOCUMENTS

| 5,604,531 | A |   | 2/1997  | Iddan et al.                |
|-----------|---|---|---------|-----------------------------|
| 5,617,451 | A |   | 4/1997  | Mimura et al.               |
| 5,830,121 | A | * | 11/1998 | Enomoto et al. ...... 600/117 |
| 6,133,884 | A | * | 10/2000 | Talvitie et al. ........ 343/702 |
| 2001/0051766 | A1 |   | 12/2001 | Gazdzinski               |
| 2004/0193020 | A1 | * | 9/2004 | Chiba et al. ........... 600/300 |
| 2005/0004473 | A1 |   | 1/2005 | Fujita et al.             |

(Continued)

FOREIGN PATENT DOCUMENTS

JP        01-245729        9/1989

(Continued)

OTHER PUBLICATIONS

Extended Supplementary European Search Report dated Nov. 30, 2009.

(Continued)

*Primary Examiner* — Dominic E Rego
(74) *Attorney, Agent, or Firm* — Scully, Scott, Murphy & Presser, P.C.

(57) ABSTRACT

To provide a receiving apparatus capable of dealing with various uses with a simple configuration. The receiving apparatus includes an antenna unit and a receiving apparatus main body. The antenna unit includes a receiving antenna that receives a radio signal including image data transmitted by a capsule endoscope inserted in a subject, and the receiving apparatus main body is detachably attached to the antenna unit. The antenna unit functions such that it demodulates the radio signal received via the receiving antenna into a baseband signal. The receiving apparatus main body acquires the image data based on at least the baseband signal.

13 Claims, 17 Drawing Sheets

U.S. PATENT DOCUMENTS

2008/0318540 A1 * 12/2008 Homan et al. ............. 455/277.1

FOREIGN PATENT DOCUMENTS

| | | |
|---|---|---|
| JP | 05-218984 | 8/1993 |
| JP | 7-231338 | 8/1995 |
| JP | H10-126295 | 5/1998 |
| JP | 2000-284957 | 10/2000 |
| JP | 2001-231186 | 8/2001 |
| JP | 2004-118308 | 4/2004 |
| JP | 2004-167163 | 6/2004 |
| JP | 2004-223113 | 8/2004 |

OTHER PUBLICATIONS

Japanese Official Action dated Apr. 6, 2010 together with English language translation.

* cited by examiner

ANTENNA UNIT AND RECEIVING APPARATUS USING THE SAME

TECHNICAL FIELD

The present invention relates to an antenna unit including a receiving antenna that receives a radio signal including image data imaged by a capsule endoscope inserted in an interior of a subject, and the present invention also relates to a receiving apparatus using the same.

BACKGROUND ART

Recently, in the field of endoscopes, a capsule endoscope, which is a swallowable endoscope, provided with an imaging function and a radio communication function emerges, and a radio in-vivo information acquiring system, which is a capsule endoscope system, that acquires in-vivo image data imaged by the capsule endoscope is under development. In this radio in-vivo information acquiring system, the capsule endoscope is swallowed from a mouth of a subject for observation (examination) and it is naturally discharged from the subject. During this time, the capsule endoscope moves in the interior of the subject such as the interior of internal organs including a stomach and a small intestine according to the peristaltic activity, and images the interior of the subject in a predetermined interval such as in an interval of 0.5 seconds.

While the capsule endoscope moves in the interior of the subject, the image data imaged by the capsule endoscope is transmitted to the exterior by a radio communication, and is received by a receiving apparatus via a receiving antenna provided outside. The receiving apparatus reconstructs the image data based on the radio signal (also called as radio frequency signal) sequentially received via the receiving antenna. Through this process, the in-vivo image data imaged by the capsule endoscope is acquired. The receiving apparatus sequentially stores the acquired image data into its memory. The subject carries the receiving apparatus having the radio communication function and the memory function so as to freely move while the subject swallows the capsule endoscope and it is naturally discharged. Thereafter, a doctor or a nurse takes out the image data stored in the memory of the receiving apparatus and inputs it to a display device. The display device then displays on its display the in-vivo image such as an image of internal organs based on the obtained image data. The doctor or the nurse uses the image of internal organs or the like displayed on the display to diagnose the subject (For example, see Patent Document 1).

Generally, such a receiving apparatus is configured to dispersely arrange on the exterior of the subject (on the surface of the subject's body, for example) a plurality of antennas that receive the radio frequency signal transmitted from the capsule endoscope and to select and switch one antenna that makes few receiving errors of the radio frequency signal so as to receive the radio signal. There has been proposed a technique in which a connector that connects a module having an antenna module assembled therein for imparting versatility to the receiving apparatus is changed so as to correspond to a plurality of interfaces (Patent Document 2).

There has been proposed another technique for keeping apart a radio controlling device and a receiving apparatus. In this technique, the receiving apparatus and the radio controlling device that controls a radio are separately built to prevent noise from entering the receiving apparatus, and the both devices are connected by a connecting cable (Patent Document 3).

Patent Document 1: Japanese Patent Application Laid-open No. 2001-231186
Patent Document 2: Japanese Patent Application Laid-open No. 2004-118308
Patent Document 3: Japanese Patent Application Laid-open No. H5-218984

DISCLOSURE OF INVENTION

Problem to be Solved by the Invention

However, the conventional receiving apparatus is built in one hardware configuration such that a received radio frequency signal is demodulated into a baseband signal, a predetermined signal process is performed based on the demodulated baseband signal so as to obtain image data, and the resultant image data is accumulated in a memory. This configuration necessitates an entire change of the receiving apparatus when the number of antennas is changed according to its examination purposes, or when the radio frequency is changed according to each service area. Each change in use requires time and labor, so that there is no flexibility.

The antenna of the receiving apparatus is often mounted on the subject. This means that the antenna and the receiving apparatus main body are coupled by a cord having a predetermined length. Accordingly, it is desired that the antenna and the receiving apparatus main body are repeatedly detachable at either unit. In this case, it is desired that the repeatedly detachable portion is not a radio-frequency connecting unit.

The antenna (more specifically, a receiving antenna) of the receiving apparatus is generally arranged on the surface of the subject, which is a position that corresponds to a moving route of the capsule endoscope, in order to receive a radio signal from the capsule endoscope inserted in the interior of the subject. The antenna is electrically connected to an antenna unit of the receiving apparatus via a cable. In this manner, when an operation for acquiring the image data of the subject by using the receiving antenna is repeatedly performed, and the number of times of using the receiving antenna increases, the operating condition of the cable that electrically connects the receiving antenna and the antenna unit gradually deteriorates, in some cases, the cable is open-circuit. In this case, it is difficult to normally receive the radio signal from the capsule endoscope inserted in the interior of the subject.

The above conventional antenna unit, however, is not configured to record the number of times of using the receiving antenna electrically connected via the cable. Thus, it is difficult to check whether the operating life of the retained receiving antenna is beyond the limit. Due to this, when the operation of receiving the radio signal from the capsule endoscope in the subject is performed, there can be a situation in which to use a receiving antenna not capable of normally receiving the radio signal because of the open-circuit of the cable, for example.

The present invention has been achieved in view of the above circumstances. A first object of the present invention is to provide a receiving apparatus capable of dealing with various uses with a simple configuration, a second object is to provide a receiving apparatus capable of preventing deterioration of the operating condition of a connector, which is caused by a repeated attaching and detaching of an antenna unit and a receiving apparatus main body, and a third object is to provide an antenna unit and a receiving apparatus using the antenna unit, capable of recording information on a usage history of all retained receiving antennas and checking whether all of these receiving antennas can normally receive a radio signal.

Means for Solving Problem

A receiving apparatus according to one aspect of the present invention includes an antenna unit including a receiving antenna that receives a radio signal including in-vivo information transmitted by a transmitting device inserted in a subject, the antenna unit demodulating the radio signal received via the receiving antenna into a baseband signal, and a receiving apparatus main body attachable to and detachable from the antenna unit, the receiving apparatus main body acquiring the in-vivo information at least based on the baseband signal.

In the receiving apparatus, the antenna unit may include a demodulator that demodulates the radio signal into the baseband signal, and a demodulation controller that controls a demodulating process of the demodulator.

In the receiving apparatus, the antenna unit and the receiving antenna may be connected so that one unit is formed.

In the receiving apparatus, the antenna unit may include a binarizing unit that binarizes the baseband signal, and a binarization controller that controls such that a binarization signal binarized by the binarizing unit is output to the receiving apparatus main body.

In the receiving apparatus, as the receiving antenna, there may be provided a plurality of antennas, and the antenna unit may include a switching unit that selects and switches one receiving antenna out of the plurality of receiving antennas, and a signal strength detector that detects a signal strength of the radio signal received by the plurality of receiving antennas.

In the receiving apparatus, the antenna unit may include a switching controller that performs a switching control of the switching unit based on the signal strength detected by the signal strength detector.

In the receiving apparatus, the demodulation controller may control such that an operation of at least the demodulator is stopped for a predetermined time when the signal strength detected by the signal strength detector does not satisfy a predetermined condition.

In the receiving apparatus, the antenna unit may include an AD converter that applies an AD conversion to a signal that corresponds to the signal strength output by the signal strength detector.

An antenna unit according to another aspect of the present invention is electrically connected in a detachable manner to a receiving apparatus main body that accumulates image data imaged by a capsule endoscope inserted in an interior of a subject, and includes at least one receiving antenna that performs a radio communication with the capsule endoscope, and the antenna unit transmits the image data received via any one of the at least one receiving antenna to the receiving apparatus main body. The antenna unit further includes a storage unit that can store usage history information on a usage history of the receiving antenna in an updatable manner.

In the antenna unit, the usage history information may include at least one of: times-of-use information indicating the number of times of using the receiving antenna; usage time information indicating a usage time of the receiving antenna; open-circuit occurrence information indicating occurrence of an open-circuit of the receiving antenna; and detection performing history information indicating a performing history of an open-circuit detection process on the receiving antenna.

In the antenna unit, the storage unit may be a nonvolatile memory.

A receiving apparatus according to still another aspect of the present invention includes one of the antenna units as described above; and a receiving apparatus main body that is electrically connected to the antenna unit in a detachable manner, receives via the antenna unit image data imaged by a capsule endoscope inserted in an interior of a subject, and accumulates the received image data.

In the receiving apparatus, the receiving apparatus main body may include a controller that controls the storage unit such that the storage unit stores the usage history information.

In the receiving apparatus, the controller may perform drive control of the receiving apparatus main body that receives the image data, and update the times-of-use information in the storage unit at every start of the drive control of the receiving apparatus main body.

In the receiving apparatus, the controller may perform drive control of the receiving apparatus main body that receives the image data, and update the usage time information in the storage unit at every time a predetermined unit time passes from a start of the drive control of the receiving apparatus main body.

In the receiving apparatus, the controller may read the usage history information in the storage unit before a start of drive control of the receiving apparatus main body, and determine whether to start the drive control of the receiving apparatus main body based on a content of the read usage history information.

In the receiving apparatus, based on each of receiving results of one or more receiving antennas retained by the antenna unit, the controller may perform an open-circuit detection process of detecting whether at least one of the one or more receiving antennas is open-circuit.

In the receiving apparatus, the controller may control the storage unit such that the storage unit stores information indicating a state of the open-circuit as the open-circuit occurrence information when the controller determines that at least one of the one or more receiving antennas is open-circuit.

In the receiving apparatus, the controller may detect the number of times of using the receiving antenna at the time that the open-circuit detection process is performed based on the times-of-use information in the storage unit, and control the storage unit such that the storage unit stores information indicating the detected number of times of use as the detection performing history information.

The receiving apparatus may include a displayer that displays warning information on the antenna unit, wherein the controller controls the displayer based on a content of the read usage history information such that the displayer displays the warning information.

In the receiving apparatus, the warning information may be one of: information for warning at least one of the one or more receiving antennas retained by the antenna unit is open-circuit; information for warning that it is necessary to perform an open-circuit detection process on the antenna unit; and information for warning that it is necessary to replace the antenna unit.

EFFECT OF THE INVENTION

According to the present invention, the receiving apparatus includes an antenna unit and a receiving apparatus main body. The antenna unit includes a demodulating unit that demodulates a received radio signal into a baseband signal, and a demodulation controller that controls a demodulation process. The receiving apparatus main body performs a process of obtaining transmission information based on at least the baseband signal. The antenna unit is detachable to the receiving apparatus main body. As a result, it is possible to realize a receiving apparatus capable of dealing with various uses with a simple configuration.

According to the present invention, the antenna unit has a function of demodulation-processing a radio signal. This prevents deterioration of the operating condition, which is caused due to a radio-frequency connection, whereby it is possible to perform a repeated attaching and detaching of the antenna unit and the receiving apparatus main body that form the receiving apparatus.

According to the present invention, it is possible to realize an antenna unit and a receiving apparatus using the antenna unit, capable of recording information on a usage history of all retained receiving antennas by each unit and easily checking whether all of these antennas can normally receive a radio signal.

EXPLANATIONS OF LETTERS OR NUMERALS

Figure 1:
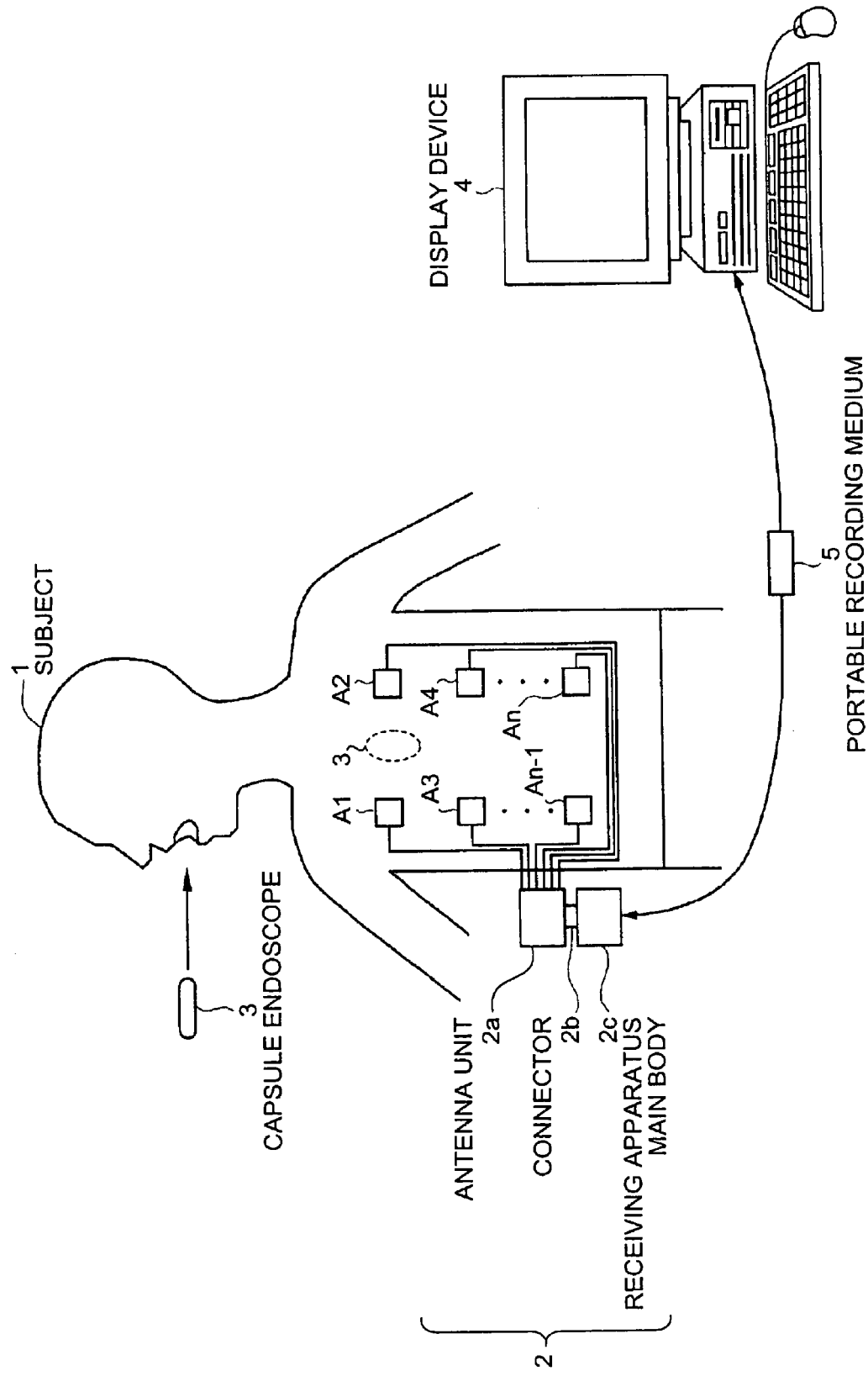
FIG. 1 is a schematic diagram showing one configuration example of a radio in-vivo information acquiring system using a receiving apparatus according to a first embodiment of the present invention.

1 Subject
2, 2A, 2B Receiving apparatus
2a, 20a, 21b Antenna unit
2b, 20b, 21b Receiving apparatus main body
2c, 20c, 21c Connector
3 Capsule endoscope
4 Display device
5 Portable recording medium
20 Demodulation controller
26, 32, 36, 42, 46 Control unit
21 Demodulating unit
22 Signal strength detecting unit
23 Antenna switching unit
27 Display unit
28 Storage unit
29 Signal processing unit
30 Binarizing controller
31 Binarizing unit
40 Switching controller
101, 102, 103 Receiving apparatus
101a, 102a, 103a Receiving apparatus main body
101b, 102b, 103b Antenna unit
101c Connector
105 Antenna
110a Control unit
110b Antenna switching unit
111a Signal processing unit
111b Demodulating unit
112a, 117b A/D converter
112b Binarizing unit
113a Display unit
113b Synchronization detector
114a Storage unit
114b Signal strength detecting unit
115a Power of receiving apparatus main body
115b Antenna unit power
118a Battery of receiving apparatus main body
118b Antenna unit battery
119a Primary side coil
119b Secondary side coil
119c Transformer
120a, 120c, 120e, 120h Light-emitting diode
120b, 120d, 120f, 120g Photodiode
121a, 121b Power unit
203 Receiving apparatus
204 Antenna unit
204a to 204d Receiving antenna
205 Receiving apparatus main body
241 Antenna switching unit
242 History storage unit
251 Power supply unit
252 Input unit
253 Display unit
254 Receiving circuit
255 Switching control circuit
256 Signal processing circuit
257 Storage unit
258 Control unit

BEST MODE(S) FOR CARRYING OUT THE INVENTION

Exemplary embodiments of an antenna unit and a receiving apparatus using the same will be explained below in detail with reference to the accompanying drawings. Note that the invention is not limited to the embodiments.

First Embodiment

FIG. 1 is a schematic diagram showing an entire configuration of a radio in-vivo information acquiring system using a receiving apparatus 2 according to the present invention. As shown in FIG. 1, the radio in-vivo information acquiring system includes a plurality of antennas A1 to An, the receiving apparatus 2, and a capsule endoscope 3. The plurality of antennas A1 to An each include a radio receiving function. The receiving apparatus 2 connects the plurality of antennas A1 to An. The capsule endoscope 3 is inserted in the body of a subject 1, images a body cavity image, and transmits by a radio frequency signal (radio signal) image data and the like to the receiving apparatus 2. Such a capsule endoscope 3 is inserted in the interior of the subject 1, has an imaging function of imaging an image inside the subject 1, and functions as a transmitting device that transmits the image data to the receiving apparatus provided outside the subject 1 via a predetermined radio wave. The radio in-vivo information acquiring system further includes a display device 4 and a portable recording medium 5. The display device 4 displays the body cavity image based on the image data received by the receiving apparatus 2. The portable recording medium 5 exchanges the data between the receiving apparatus 2 and the display device 4. The receiving apparatus 2 includes an antenna unit 2a and a receiving apparatus main body 2b. The antenna unit 2a connects the plurality of antennas A1 to An and processes the radio signal received via the plurality of antennas A1 to An. The receiving apparatus main body 2b acquires the image data based on the radio signal processed by the antenna unit 2a. The antenna unit 2a and the receiving apparatus main body 2b are connected by a connector 2c.

The capsule endoscope 3 has an imaging function of imaging the interior of the subject 1, and a radio communication function of transmitting to the receiving apparatus 2 the image data obtained by imaging the interior of the subject 1. The capsule endoscope 3 is swallowed by the subject 1, passes an esophagus inside the subject 1, and moves through the body cavity according to peristalsis of the lumen of a digestive tract. At the same time, the capsule endoscope 3 sequentially images an image in the body cavity of the subject 1, and sequentially transmits the obtained image data inside the subject 1 to the receiving apparatus 2.

The display device 4 displays the image and the like inside the subject 1 imaged by the capsule endoscope 3. The display device 4 has a configuration like a workstation that displays the image based on the data obtained via the portable recording medium 5, for example. More specifically, the display device 4 can be configured to directly display the image by using a CRT display, a liquid crystal display, for example. The display device 4 can also be configured to output the image to another medium such as a printer. The display device 4 also has a processing function of a doctor or a nurse to perform a diagnosis based on the image such as an internal organ in the subject imaged by the capsule endoscope 3.

The mobile recording medium 5 is detachable to the receiving apparatus main body 2b and the display device 4. The portable recording medium 5 has a structure capable of outputting or recording information when the portable recording medium 5 is attached to the both units. More specifically, the portable recording medium 5 is a recording medium that can be carried such as a Compact Flash (registered trademark) or a smart media. The portable recording medium 5 is attached to the receiving apparatus main body 2b and records the data transmitted from the capsule endoscope 3 while the capsule endoscope 3 moves through the body cavity of the subject 1. After the capsule endoscope 3 is discharged from the subject 1, that is, after the capsule endoscope 3 completes imaging the interior of the subject 1, the portable recording medium 5 is taken out from the receiving apparatus main body 2b and attached to the display device 4. The data is read by the display device 4. As a result of exchanging the data between the receiving apparatus main body 2b and the display device 4 by using such a portable recording medium 5, the subject 1 can move more freely while the body cavity of the subject 1 is imaged compared to the case that the receiving apparatus main body 2b and the display device 4 are connected by wire. This type of data exchange also contributes to shortening of a period during which the data is exchanged to the display device 4. Although the portable recording medium 5 is used to exchange the data between the receiving apparatus main body 2b and the display device 4, the data exchange is not always limited thereto. For example, another built-in recording device, which is used as the receiving apparatus main body 2b, and the display device 4 can be connected by wire or by radio to exchange the data between the both units.

Figure 2:
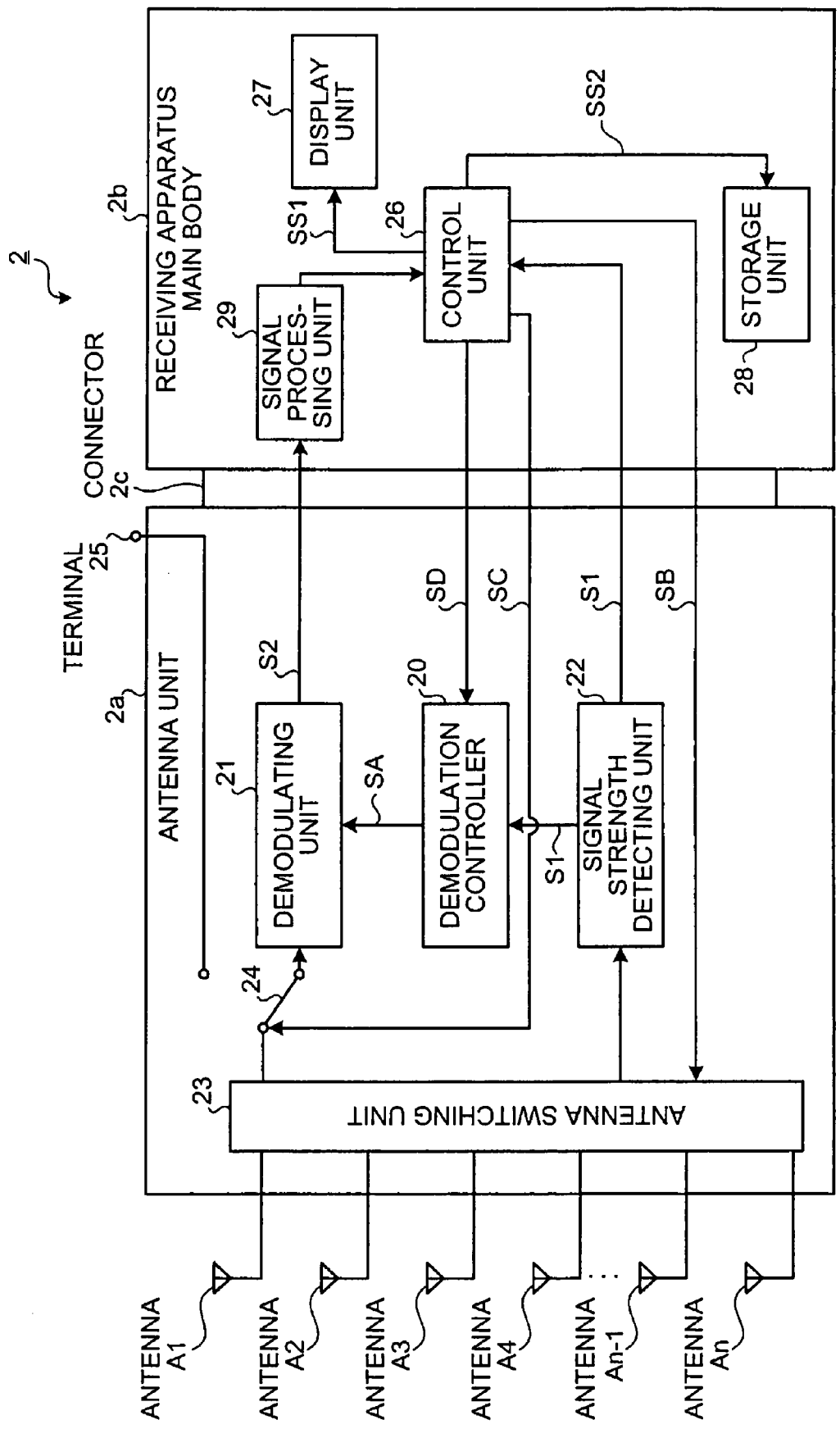
FIG. 2 is a block diagram showing a schematic configuration of the receiving apparatus according to the first embodiment of the present invention.

The receiving apparatus 2 is explained below with reference to FIG. 2. FIG. 2 is a block diagram showing a schematic configuration of the receiving apparatus according to a first embodiment of the present invention. As shown in FIG. 2, the receiving apparatus 2 has the receiving apparatus main body 2b, and an antenna unit 2a that connects the above plurality of antennas A1 to An. The antenna unit 2a and the receiving apparatus main body 2b are connected by the connector 2c. The antenna unit 2a includes a demodulation controller 20 and a demodulating unit 21 that demodulate a received radio frequency signal into a baseband signal S2. Accordingly, even when the number of antennas is changed or when the signal is receiving with different radio frequencies, the receiving apparatus main body 2b can input the similar baseband signal S2 by replacing the antenna unit 2a.

The receiving apparatus 2 is explained next in detail. The antenna unit 2a includes an antenna switching unit 23, the demodulating unit 21, a signal strength detecting unit 22, a switch 24, and the terminal 25. The antenna switching unit 23 connects and switches the plurality of antennas A1 to An. The demodulating unit 21 demodulates the radio frequency signal received via the antenna switching unit 23. The demodulation controller 20 controls a demodulation operation of the demodulating unit 21. The signal strength detecting unit 22 detects a signal strength of the radio frequency signal input from the antenna switching unit 23 (that is, a received strength of the radio signal received by any one of the plurality of antennas A1 to An). The switch 24 outputs the radio frequency signal input via the antenna switching unit 23 to either the demodulating unit 21 or the terminal 25. The terminal 25 is connected to the switch 24. The switch 24 is switched and the radio frequency signal is monitored by the terminal 25, whereby a trouble area of the antenna unit 2a can be diagnosed.

The antenna switching unit 23 of the antenna unit 2a outputs to the signal strength detecting unit 22 the radio frequency signal received via the plurality of antennas A1 to An. The signal strength detecting unit 22 detects the signal strength of the input radio frequency signal, and outputs an antenna strength signal S1 to the receiving apparatus main body 2*b*. The antenna switching unit 23 is input a switching signal SB, selects one antenna out of the plurality of antennas A1 to An, and outputs to the demodulating unit 21 via the switch 24 the radio frequency signal received by the selected antenna. The demodulating unit 21 demodulates the radio frequency signal into the baseband signal S2 based on a control signal SA input from the demodulation controller 20, and outputs the baseband signal S2 to the receiving apparatus main body 2*b*. The demodulation controller 20 is input a control signal SD from the receiving apparatus main body 2*b*. When the control signal SD instructs start of activation, the demodulation controller 20 controls a demodulation operation of the demodulating unit 21 with the control signal SA. A switching operation of the switch 24 is controlled by a control signal SC. The switch 24 outputs the radio frequency signal input via the antenna switching unit 23 by selecting the demodulating unit 21 side or the terminal 25 side.

The receiving apparatus main body 2*b* includes a signal processing unit 29, a storage unit 28, a display unit 27, and a control unit 26. The signal processing unit 29 performs a signal process in which the baseband signal S2 demodulated by the antenna unit 2*a* is input, and the baseband signal S2 is converted into a digital signal so as to generate the image data. The storage unit 28 stores at least the image data. The display unit 27 displays and outputs various pieces of information. The control unit 26 controls each of the above units and performs drive control on the antenna unit 2*a*.

The control unit 26 of the receiving apparatus main body 2*b* outputs the switching signal SB to the antenna unit 2*a* based on the input antenna strength signal S1, and controls a selecting operation of the antenna by the antenna switching unit 23. The control unit 26 outputs the control signal SD to the antenna unit 2*a* so that the demodulating unit 21 starts the demodulation operation, and acquires the image data from an output of the signal processing unit 29. The control unit 26 outputs an image signal SS1 to the display unit 27, and outputs a data signal SS2 including the image data to the storage unit 28. The display unit 27 is input the image signal SS1, and displays the image data. The storage unit 28 is input the data signal SS2, and stores the image data.

Figure 3:
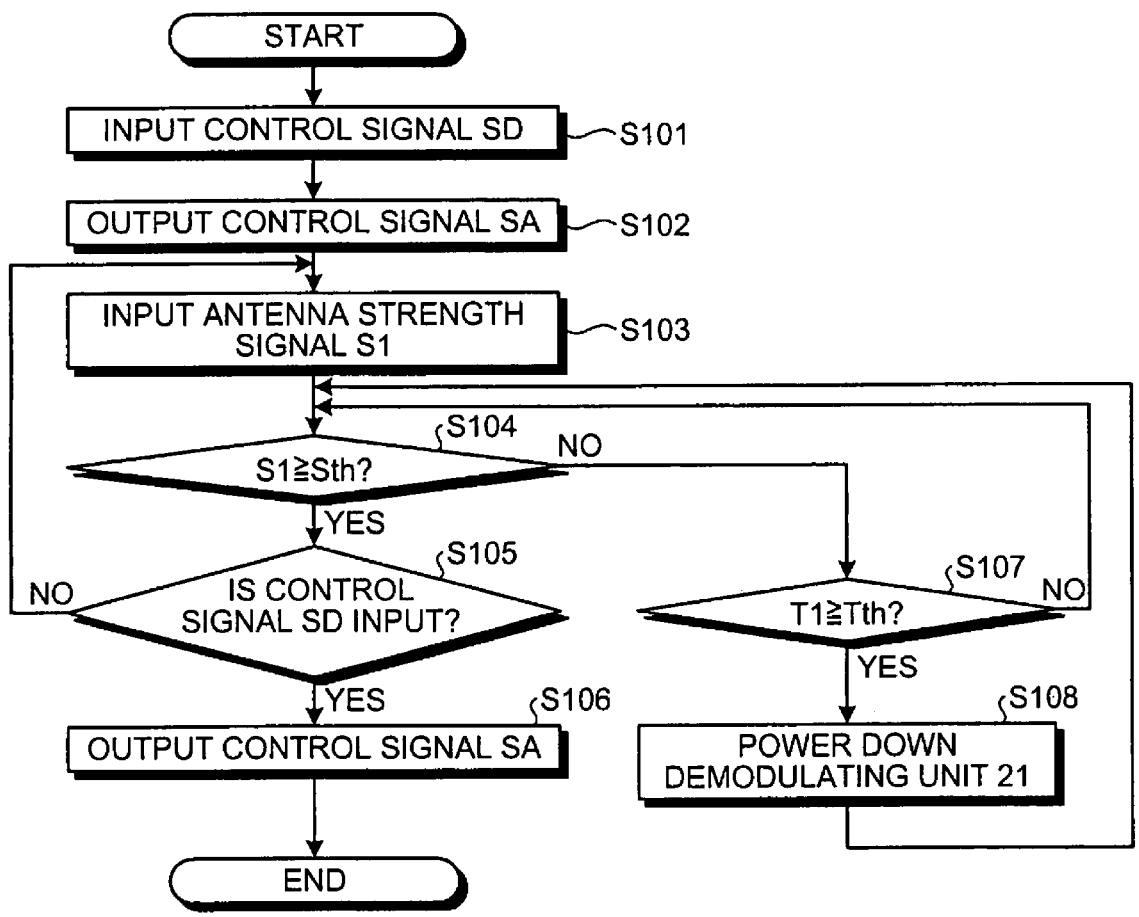
FIG. 3 is a flowchart showing an operation of a demodulation controller according to the first embodiment of the present invention.

An operation of the demodulation controller 20 of the antenna unit 2*a* is explained next with reference to a flowchart shown in FIG. 3. First, the demodulation controller 20 is input the control signal SD from the control unit 26 provided in the receiving apparatus main body 2*b* (step S101). When the control signal SD instructs the start of activation, the demodulation controller 20 outputs the control signal SA to the demodulating unit 21 (step S102), and starts the demodulation operation of the demodulating unit 21 and performs the demodulation control. The demodulating unit 21 demodulates the radio frequency signal input via the antenna switching unit 23, and outputs the baseband signal S2. The demodulation controller 20 is also input the antenna strength signal S1 from the signal strength detecting unit 22 (step S103), and determines whether the signal strength of the antenna strength signal S1 is greater than a predetermined threshold value Sth (step S104). When the signal strength of the antenna strength signal S1 is greater than the threshold value Sth (step S104, Yes), the demodulation controller 20 continues the demodulation control, and determines whether the demodulation controller 20 is input from the control unit 26 with the control signal SD that instructs stop of activation (step S105). When the demodulation controller 20 is input the control signal SD that instructs the stop of activation from the control unit 26 (step S105, Yes), the demodulation controller 20 outputs the control signal SA to the demodulating unit 21 (step S106) and ends the demodulation operation of the demodulating unit 21.

In contrast, when the antenna strength signal S1 is not greater than the threshold value Sth (step S104, No), the demodulation controller 20 measures a time T1 at which the antenna strength signal S1 is not greater than the threshold value Sth, and determines whether the time T1 is greater than a threshold time Tth (step S107). When the time T1 is greater than the threshold time Tth (step S107, Yes), the demodulation controller 20 outputs the control signal SA to the demodulating unit 21 and performs a power down of the demodulating unit 21 for a predetermined time (step S108). Therefore, the demodulating unit 21 stops the demodulation operation during this predetermined time, whereby electric power saving is made possible.

In the first embodiment, the antenna unit 2*a* includes the demodulation controller 20 and the demodulating unit 21, and outputs the demodulated baseband signal S2 to the receiving apparatus main body 2*b*. Thus, when the receiving apparatus 2 is used by changing the number of antennas according to varying situations of the subject 1, for example, the same receiving apparatus main body 2*b* can be used by replacing the antenna unit 2*a* by an antenna unit 2*a* having the number of antennas that corresponds to the varying situations.

When the receiving apparatus 2 is used in an area where the radio frequency is changed, for example, the same receiving apparatus main body 2*b* can be used by replacing the antenna unit 2*a* by an antenna unit 2*a* of which radio frequency is changed accordingly.

As explained above, the receiving apparatus 2 can be detachably separated into the antenna unit 2*a* and the receiving apparatus main body 2*b*. Each antenna unit 2*a* itself performs the demodulation control by the demodulation controller 20 that corresponds to the demodulating unit 21, and can be connected by the baseband signal S2 common to the receiving apparatus main body 2*b* for communication. Accordingly, this increases the versatility of the receiving apparatus main body 2*b* with respect to the antenna unit 2 designed in various uses, and leads to a simple configuration of the receiving apparatus main body 2*b*.

The signals that undergo the connector 2*c* are converted into the baseband signals in low frequency. Thus, no noise penetrates via the connector 2*c*, whereby the receiving apparatus 2 can acquire good image data.

The demodulation controller 20 is configured to perform the power down of the demodulating unit 21 when the signal strength of the received radio frequency signal is less than the predetermined strength and continues for the predetermined time or longer. This configuration leads to power-saving, and provides a prolonged operating time of the receiving apparatus 2.

Although in the first embodiment, the selecting operation of the switch 24 is performed by the control signal SC from the receiving apparatus main body 2*b*, the selecting operation can be performed manually. The demodulation controller 20 is configured to perform the power down of the demodulating unit 21 based on the signal strength of the antenna strength signal S1. The power down of the demodulating unit 21, however, can be performed as follows: the baseband signal S2 is input and the power down is performed based on the level of the baseband signal S2.

Second Embodiment

A second embodiment of the present invention is explained next. In the first embodiment, the demodulation controller 20 is arranged in the antenna unit 2a, and the antenna unit 2a performs the demodulation control. In the second embodiment, a binarizing unit that converts a baseband signal into a digital baseband signal is provided in an antenna unit 20a. A control unit that controls the binarizing unit is arranged also on the antenna unit 20a side.

Figure 4:
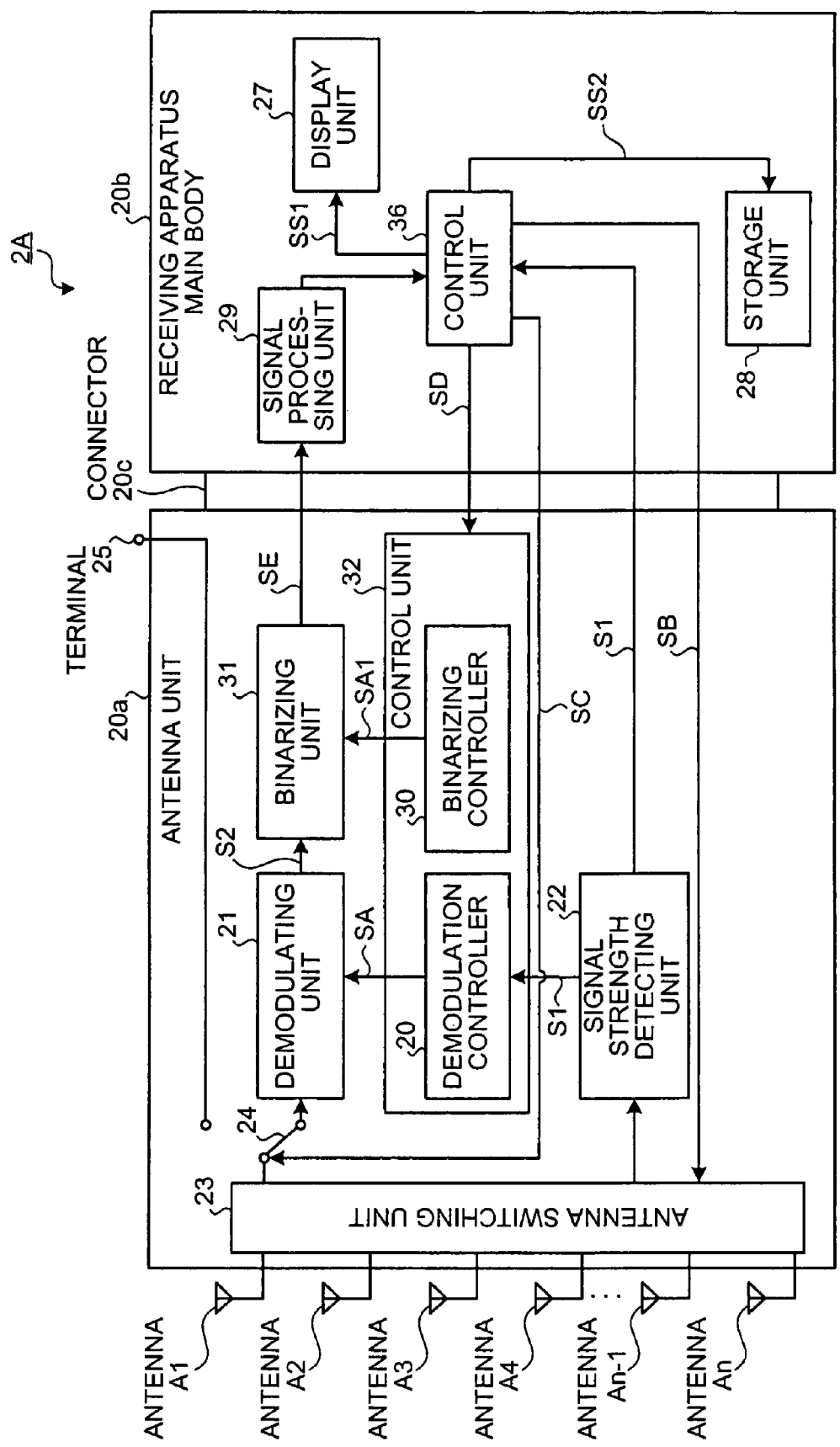
FIG. 4 is a block diagram showing a schematic configuration of a receiving apparatus according to a second embodiment of the present invention.

FIG. 4 is a block diagram showing a schematic configuration of a receiving apparatus 2A according to the second embodiment. As shown in FIG. 4, the receiving apparatus 2A includes the antenna unit 20a and a receiving apparatus main body 20b. These units replace the antenna unit 2a and the receiving apparatus main body 2b of the above receiving apparatus 2 according to the first embodiment. The antenna unit 20a and the receiving apparatus main body 20b are detachably connected by a connector 20c, similarly to the above connector 2c. The antenna unit 20a further includes a binarizing unit 31 and a binarizing controller 30. The binarizing unit 31 converts an analog baseband signal S2 output from the demodulating unit 21 into a baseband signal SE, which is a digital signal. The binarizing controller 30 performs a binarization control on the binarizing unit 31. A control unit 32 integrally controls the demodulation controller 20 and the binarizing controller 30. The receiving apparatus main body 20b does not need to binarize the signal and directly performs a signal process of generating image data because the input baseband signal is the digital baseband signal SE. Other configurations are the same as those of the receiving apparatus 2 shown in the first embodiment, and like parts are designated by like reference letters or numerals.

In the receiving apparatus 2A, the antenna unit 20a and the receiving apparatus main body 20b are connected by the digital baseband signal SE so that communication is established therebetween. Thus, the receiving apparatus 2A is relatively not affected by noise, so that good image data can be generated.

Figure 5:
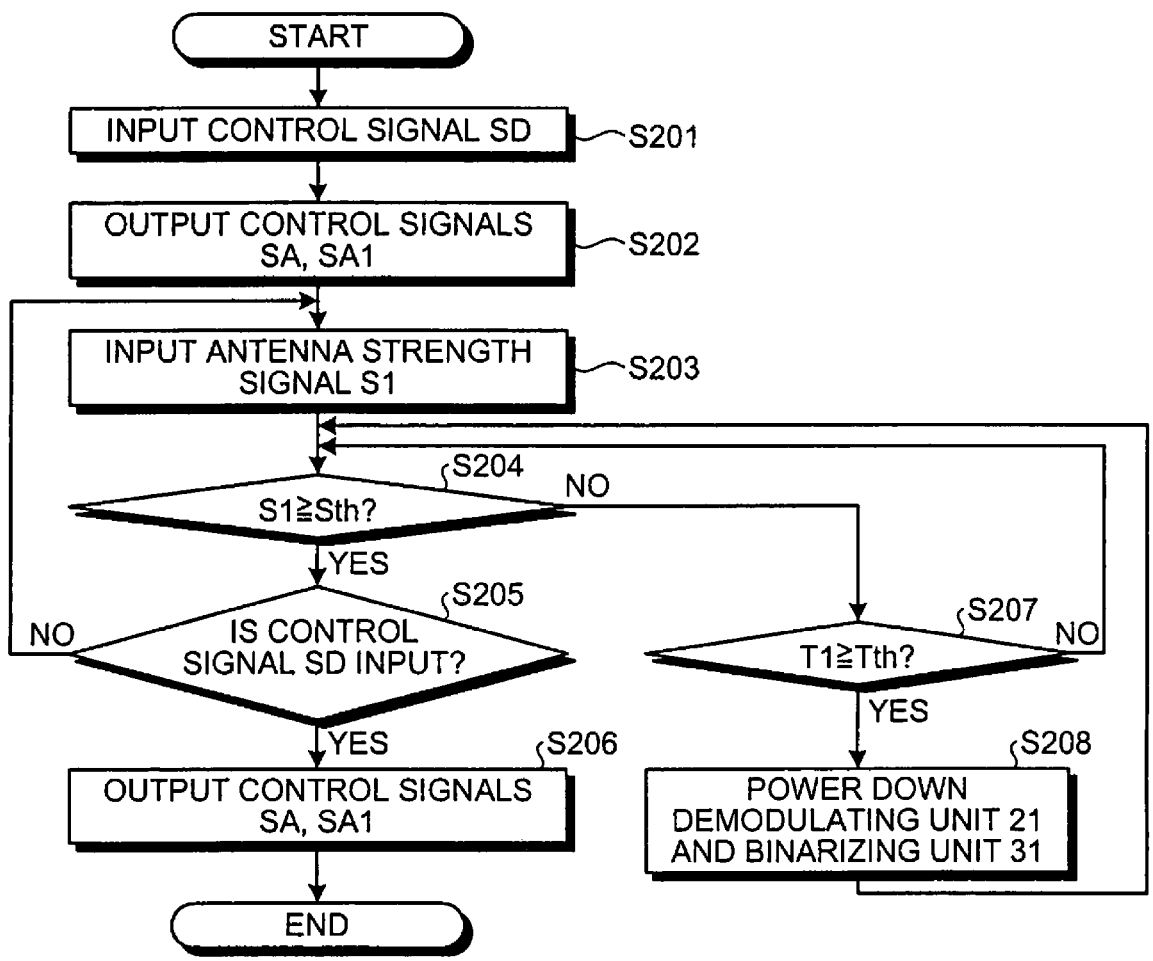
FIG. 5 is a flowchart showing an operation of a control unit according to the second embodiment of the present invention.

An operation of the control unit 32 is explained below with reference to a flowchart shown in FIG. 5. First, the control unit 32 is input a control signal SD from the receiving apparatus main body 20b (more specifically, from a control unit 36) (step S201). When the control signal SD instructs start of activation, the control unit 32 outputs a control signal SA to the demodulating unit 21 and outputs a control signal SA1 to the binarizing unit 31 (step S202). In this case, the demodulation controller 20 outputs the control signal SA to the demodulating unit 21 such that the demodulating unit 21 starts a demodulation operation. The binarizing controller 30 outputs the control signal SA1 to the binarizing unit 31 such that the binarizing unit 31 starts a binarization operation. The demodulating unit 21 demodulates the radio frequency signal input via the antenna switching unit 23 and outputs the baseband signal S2 to the binarizing unit 31. The demodulation controller 20 is input an antenna strength signal S1 from the signal strength detecting unit 22 (step S203), and determines whether the signal strength of the antenna strength signal S1 is greater than a predetermined threshold value Sth (step S204). When the signal strength of the antenna strength signal S1 is greater than the threshold value Sth (step S204, Yes), the demodulation controller 20 continues the demodulation control, and determines whether the control signal SD that instructs stop of activation is input (step S205). When the control unit 32 is input the control signal SD that instructs the stop of activation (step S205, Yes), the control unit 32 outputs the control signal SA to the demodulating unit 21 and outputs the control signal SA1 to the binarizing unit 31 (step S206). In this case, the demodulation controller 20 outputs the control signal SA to the demodulating unit 21 such that the demodulating unit 21 ends the demodulation operation. The binarizing controller 30 outputs the control signal SA1 to the binarizing unit 31 such that the binarizing unit 31 ends the binarization operation.

In contrast, when the antenna strength signals S1 of all the antennas are not greater than the threshold value Sth (step S204, No), the control unit 32 measures a time T1 at which the antenna strength signal S1 is not greater than the threshold value Sth, and determines whether the time T1 is more than a predetermined threshold time Tth (step S207). When the time T1 is more than the threshold time Tth (step S207, Yes), the demodulation controller 20 outputs the control signal SA to the demodulating unit 21, and performs a power down of the demodulating unit 21 for a predetermined time. The binarizing controller 30 outputs the control signal SA1 to the binarizing unit 31 and performs a power down of the binarizing unit 31 for a predetermined time (step S208).

In the second embodiment, the antenna unit 20a is configured to binarize the demodulated baseband signal S2 and output the digital signal SE to the receiving apparatus main body 20b, so that the antenna unit 20a and the receiving apparatus main body 20b are connected for communication by the digital baseband signal SE, whereby it is possible to acquire good image data that contains only an insignificant amount of noise. In this case also, the binarizing controller 30 is provided on the antenna unit 20a side. Thus, the versatility of the receiving apparatus main body 20b is improved with respect to the antenna unit 20a designed in various uses, similarly to the above the first embodiment, whereby the configuration of the receiving apparatus main body 20b is rendered simple, and the versatility of the receiving apparatus can be increased.

Note that, in the second embodiment, although the power down process is performed by using the antenna strength signal S1, the power down process can be performed by using a fixed pattern included in the digital baseband signal SE. The power down process of the demodulating unit 21 and the power down process of the binarizing unit 31 can be performed separately.

Third Embodiment

A third embodiment of the present invention is explained next. In the first and second embodiments, the antenna units 2a and 20a demodulate the radio frequency signal into the baseband signals S2 and SE. In the third embodiment, an antenna switching control is further performed on the antenna unit side.

Figure 6:
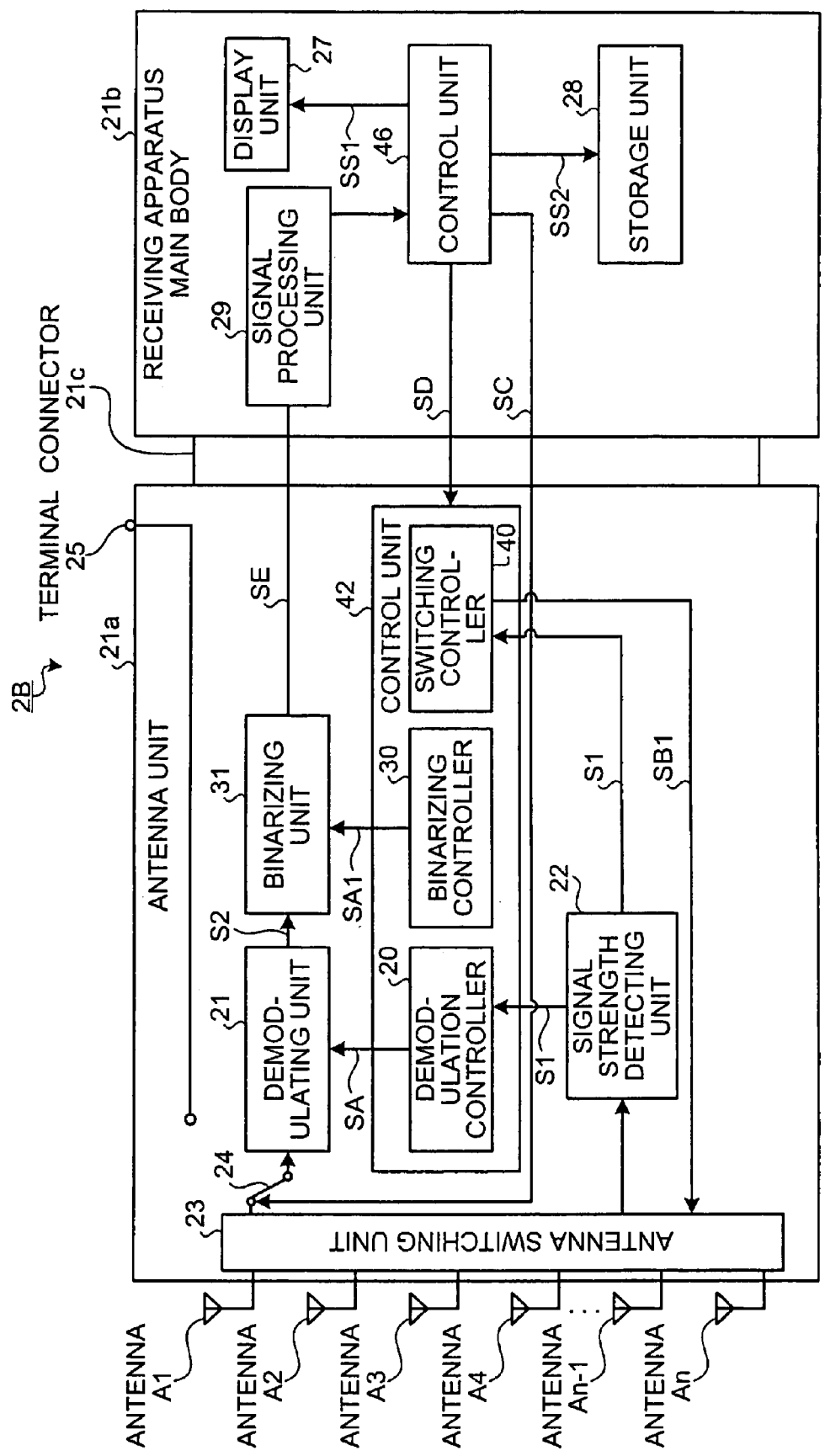
FIG. 6 is a block diagram showing a schematic configuration of a receiving apparatus according to a third embodiment of the present invention.

FIG. 6 is a block diagram showing a schematic configuration of a receiving apparatus 2B according to the third embodiment. As shown in FIG. 6, the receiving apparatus 2B includes an antenna unit 21a and a receiving apparatus main body 21b. These units replace the antenna unit 20a and the receiving apparatus main body 20b of the above receiving apparatus 2A according to the second embodiment. The antenna unit 21a and the receiving apparatus main body 21b are detachably connected by a connector 21c, similarly to the above connector 20c. On the antenna unit 21a side, there is further provided a switching controller 40 that performs a switching control of the antennas A1 to An based on the antenna strength signal S1 detected by the signal strength detecting unit 22.

The antenna switching unit 23 selects the antennas A1 to An according to a switching signal SB1 from the switching controller 40. A control unit 46 on the receiving apparatus main body 21b side does not perform a switching control that corresponds to the switching controller 40. Other configurations are the same as that in the second embodiment. Like parts are designated by like reference letters or numerals.

Figure 7:
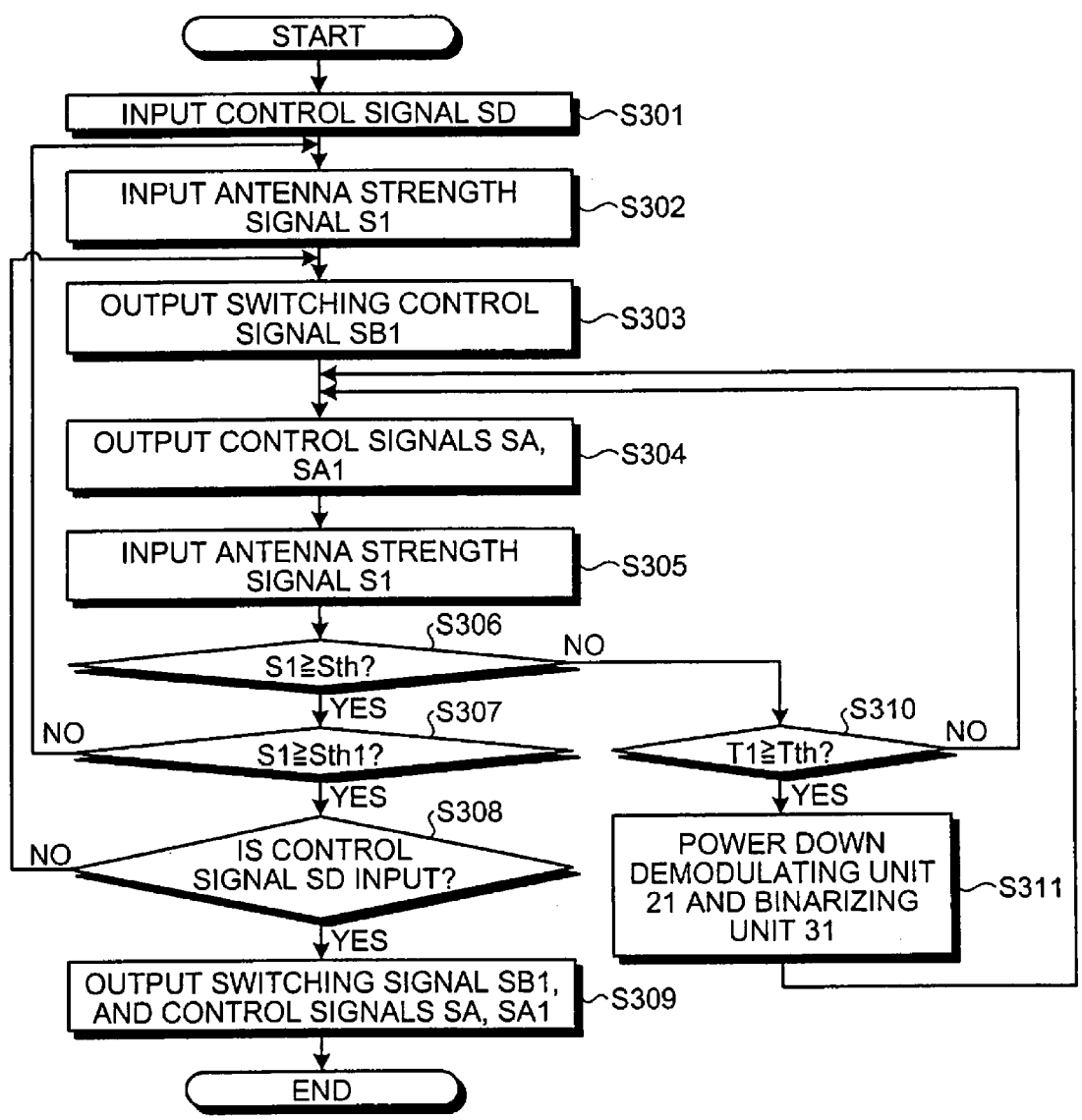
FIG. 7 is a flowchart showing an operation of a control unit according to the third embodiment of the present invention.

An operation of the control unit 42 of the antenna unit 21*a* is explained below with reference to a flowchart shown in FIG. 7. First, the control unit 42 is input a control signal SD from the receiving apparatus main body 21*b* (more specifically, from a control unit 46) (step S301). When the control signal SD instructs start of activation, the switching controller 40 is input the antenna strength signal S1 from the signal strength detecting unit 22 (step S302), and outputs the switching signal SB1 for selecting an antenna of which receiving strength is the strongest out of a plurality of antennas A1 to An, based on the antenna strength signal S1 (step S303). The demodulation controller 20 outputs the control signal SA to the demodulating unit 21 so that the demodulating unit 21 starts a demodulation operation. The binarizing controller 30 outputs the control signal SA1 to the binarizing unit 31 such that the binarizing unit 31 starts a binarization operation (step S304).

The demodulating unit 21 is input and demodulates the radio frequency signal via the antenna switched by the switching controller 40, and outputs a baseband signal S2 to the binarizing unit 31. The demodulation controller 20 is input the antenna strength signal S from the signal strength detecting unit 22 (step S305), and determines whether the signal strength of the antenna strength signal S1 is greater than a predetermined threshold value Sth (step S306). When the signal strength of the antenna strength signal S1 is greater than the threshold value Sth (step S306, Yes), the switching controller 40 determines whether the antenna strength signal S1 is greater than a predetermined threshold value Sth1 (step S307). When the antenna strength signal S1 is greater than the threshold value Sth1 (step S307, Yes), the demodulation controller 20 continues the demodulation control and determines whether the demodulation controller 20 is input the control signal SD that instructs stop of activation from the control unit 46 (step S308). When the control unit 42 is input the control signal SD that instructs the stop of activation (step S308, Yes), the control unit 42 outputs the switching signal SB1 to the antenna switching unit 23, outputs the control signal SA to the demodulating unit 21, and outputs the control signal SA1 to the binarizing unit 31 (step S309). In this case, the switching controller 40 outputs the switching signal SB1 to the antenna switching unit 23 so that the antenna switching unit 23 ends the switching operation of the antenna switching unit 23. The demodulation controller 20 outputs the control signal SA to the demodulating unit 21 so that the demodulating unit 21 ends the demodulation operation. The binarizing controller 30 outputs the control signal SA1 to the binarizing unit 31 so that the binarizing unit 31 ends the binarizing operation.

On the other hand, when the antenna strength signals S1 of all the antennas are not greater than the threshold value Sth (step S306, No), the demodulation controller 20 measures a time T1 at which the antenna strength signal S1 is not greater than the threshold value Sth, and determines whether the time T1 is greater than a predetermined threshold time Tth (step S310). When the time T1 is greater than the threshold time Tth (step S310, Yes), the demodulation controller 20 outputs the control signal SA to the demodulating unit 21, and performs a power down of the demodulating unit 21 for a predetermined time. The binarizing controller 30 outputs the control signal SA1 to the binarizing unit 31, and performs a power down of the binarizing unit 31 for a predetermined time (step S311).

When the antenna strength signal S1 is not greater than the threshold value Sth1 (step S307, No), the switching controller 40 repeats the process procedures from the step S302 and onward to perform the switching control of the antenna.

In the third embodiment, the antenna unit 21*a* further includes the switching controller 40. The switching controller 40 is configured to control the switching operation of the antenna switching unit 23 based on the antenna strength signal S1. Therefore, the effects of the second embodiment are embraced also in the third embodiment. It is not necessary to make various control settings when the number of antennas is changed, whereby the configuration of the receiving apparatus main body 21 is simplified, and a common configuration of the antenna unit and the receiving apparatus is made possible.

In the third embodiment, although the determination of whether to perform the power down is made before the determination of the antenna switching, the determination of the antenna switching can be performed before the determination of whether to perform the power down.

In the third embodiment, although the determination of whether to perform the power down and the determination of the antenna switching are made based on different references, the same reference can be used to make the determination.

Fourth Embodiment

A fourth embodiment of the present invention is explained next in detail. A receiving apparatus according to the fourth embodiment includes an antenna unit and a receiving apparatus main body. The antenna unit includes a demodulation process function of demodulating a radio signal received from the capsule endoscope 3. The antenna unit and the receiving apparatus main body are detachably connected by a low-frequency signal connector, whereby deterioration of the condition of the connector, which is caused due to attaching and detaching of the antenna unit and the receiving apparatus main body, is prevented.

Figure 8:
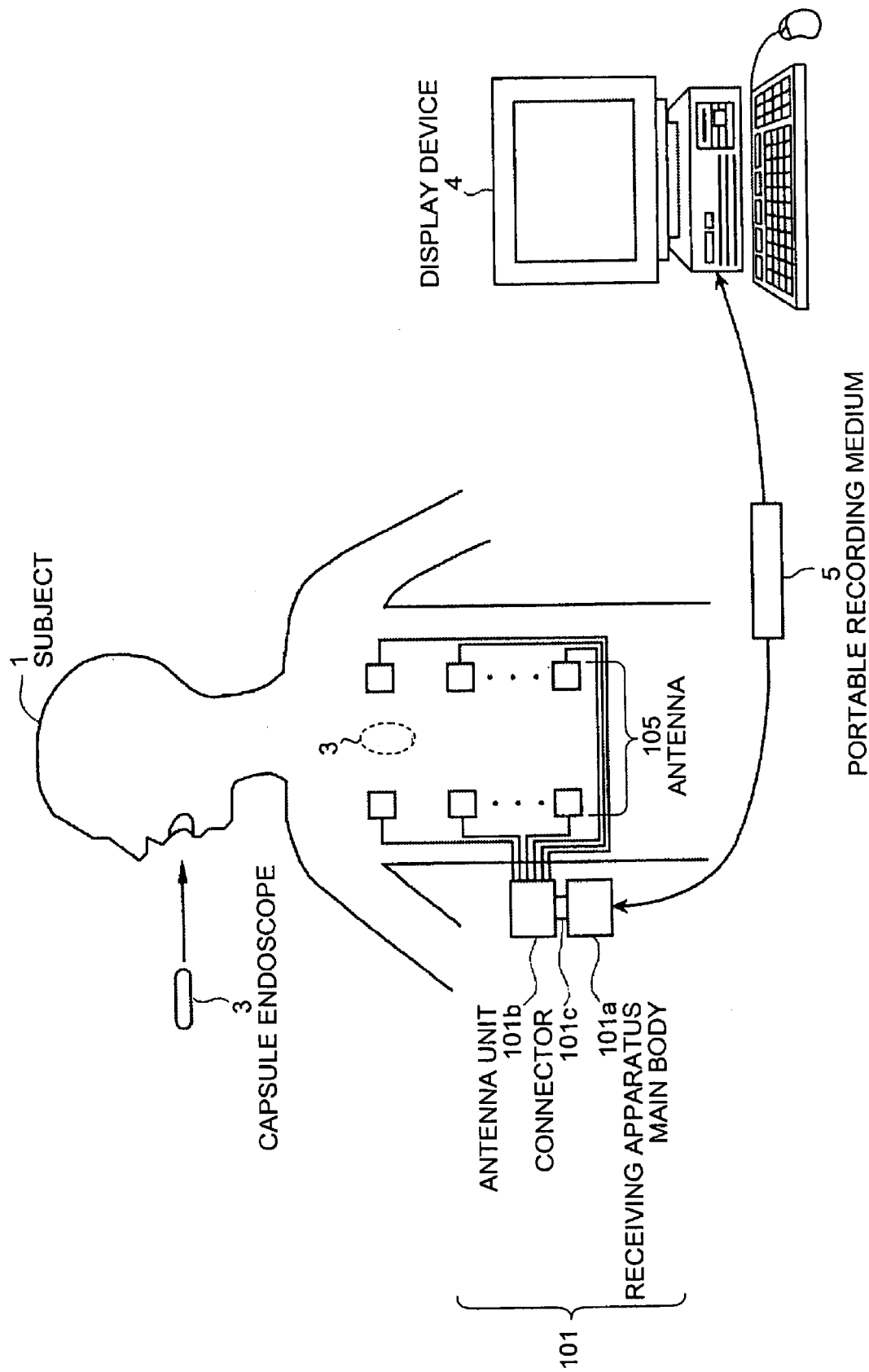
FIG. 8 is a schematic diagram showing one configuration example of a radio in-vivo information acquiring system using a receiving apparatus according to a fourth embodiment of the present invention.

FIG. 8 is a schematic diagram showing an entire configuration of a radio in-vivo information acquiring system using a receiving apparatus according to the present invention. As shown in FIG. 8, the radio in-vivo information acquiring system includes a plurality of antennas 105, a receiving apparatus 101, and a capsule endoscope 3. The plurality of antennas 105 each include a radio receiving function. The receiving apparatus 101 connects the plurality of antennas 105. The capsule endoscope 3 is inserted in the body of the subject 1, images a body cavity image, and transmits by a radio frequency signal the image data and the like to the receiving apparatus 101. The radio in-vivo information acquiring system further includes a display device 4 and a portable recording medium 5. The display device 4 displays the body cavity image based on the image data received by the receiving apparatus 101. The portable recording medium 5 exchanges data between the receiving apparatus 101 and the display device 4. The receiving apparatus 101 includes an antenna unit 101*b* and a receiving apparatus main body 101*a*. The antenna unit 101*b* is connected to a plurality of antennas 105, and demodulates the radio frequency signal received via the plurality of antennas 105*a*. The receiving apparatus main body 101*a* acquires the image data based on a baseband signal demodulated by the antenna unit 101*b*. The antenna unit 101*b* and the receiving apparatus main body 101*a* are connected by a connector 110*c*.

The display device 4 displays the image inside the subject 1 (a body cavity image, for example) imaged by the capsule endoscope 3, as explained above. The portable recording medium 5 exchanges the data between the receiving apparatus and the display device 4 of the radio in-vivo information acquiring system according to the present invention, as explained above. In the fourth embodiment, the portable recording medium 5 is detachable to the receiving apparatus main body 101*a* and the display device 4, is attached to the receiving apparatus main body 101*a*, and records the data transmitted from the capsule endoscope 3 while the capsule endoscope 3 moves through the body cavity of the subject 1. After the capsule endoscope 3 is discharged from the subject 1, that is, after the capsule endoscope 3 completes imaging the interior of the subject 1, the portable recording medium 5 is taken out from the receiving apparatus main body 101*a* and attached to the display device 4. The recorded data is read by the display device 4. When the data exchange is performed between the receiving apparatus main body 101*a* and the display device 4 by using the portable recording medium 5, the subject 1 can move more freely while body cavity of the subject 1 is imaged, compared to the case that the receiving apparatus main body 101*a* and the display device 4 are connected by wire. This type of data exchange also contributes to shortening of a period during which the data is exchanged to the display device 4.

Although the portable recording medium 5 is used for exchanging the data between the receiving apparatus main body 101*a* and the display device 4, the data exchange is not always limited thereto. Another built-in recording device, which is used as the receiving apparatus main body 101*a*, and the display device 4 can be connected by wire or by radio to exchange the data between the both units.

Figure 9:
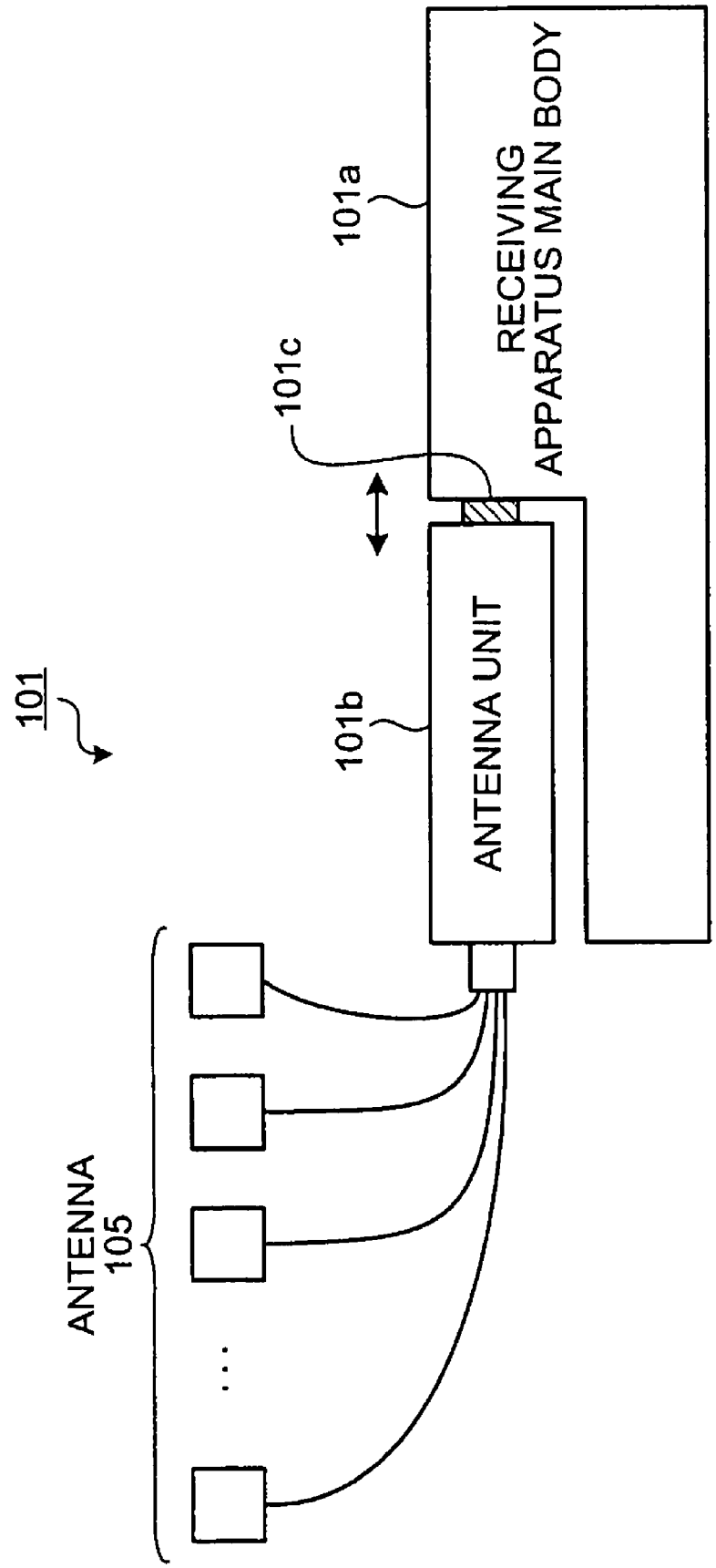
FIG. 9 is a cross-sectional view showing the appearance of the receiving apparatus according to the fourth embodiment of the present invention.

The detailed configuration of the receiving apparatus 101 is explained with reference to FIG. 9 and FIG. 10. As shown in FIG. 9, the receiving apparatus 101 includes the receiving apparatus main body 101*a* and the antenna unit 101*b*. The antenna unit 101*b* is electrically connected to the receiving apparatus main body 101*a* by the connector 101*c* so as to be physically fixed. The antenna unit 101*b* connects a plurality of antennas 105. The plurality of antennas 105 are fixed onto the subject 1 (not shown). In this case, the antenna unit 101*b* and the plurality of antennas 105 are connected so that one unit is formed. Thus, the plurality of antennas 105 are not detachable to the antenna unit 101*b*. That is, when the plurality of antennas 105 of the receiving apparatus 101 are replaced by another antenna, the antenna unit 101*b* is taken out from the receiving apparatus main body 101*a* and the plurality of antennas 105 are replaced together with the antenna unit 101*b*. The connector 101*c* is configured of a plug and a socket. One of the plug and the socket is attached to the antenna unit 101*b*, and the other is attached to the receiving apparatus main body 101*a*. The antenna unit 101*b* is easily detached from the receiving apparatus main body 101*a* via the connector 101*c*.

Figure 10:
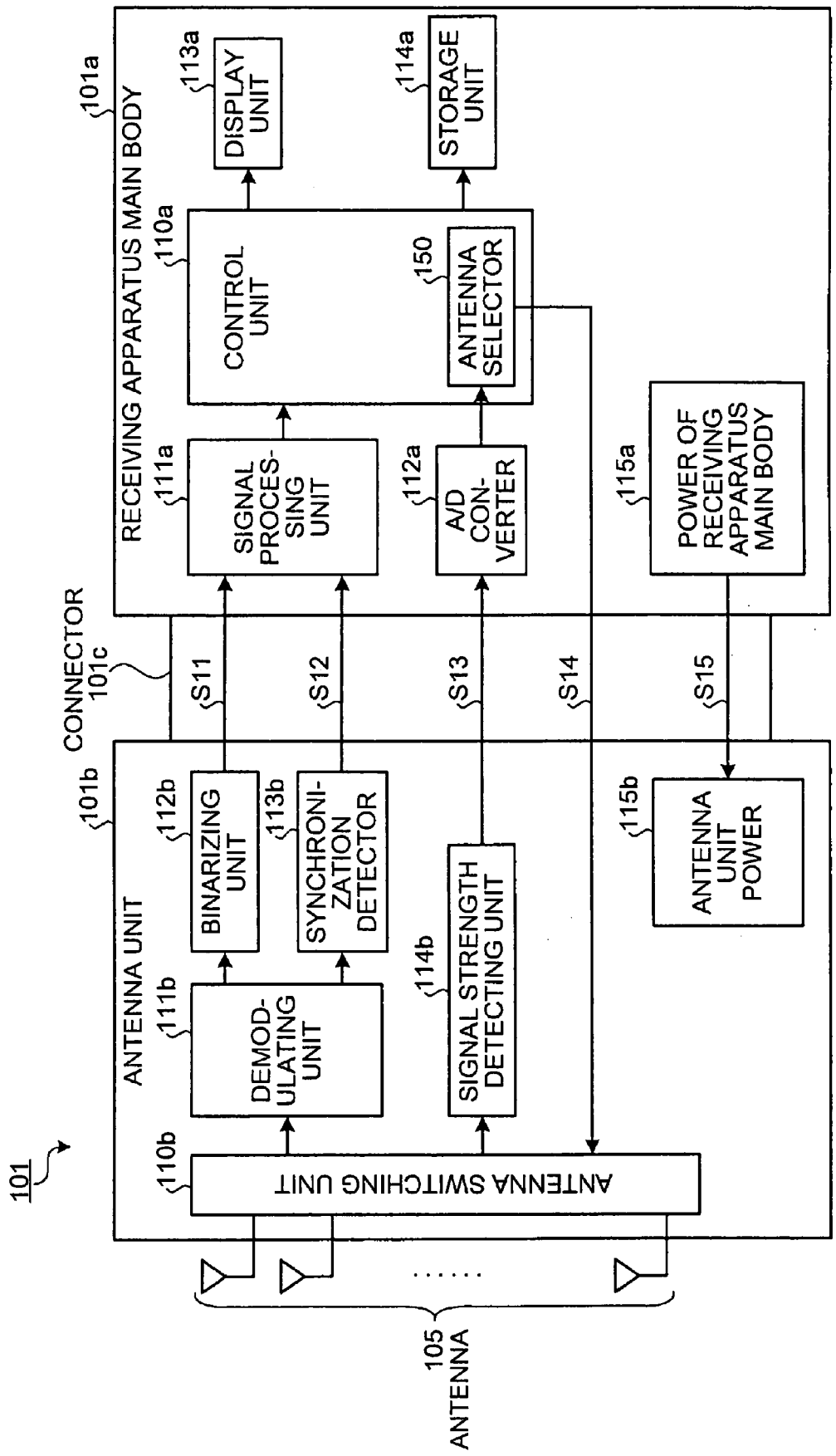
FIG. 10 is a block diagram showing a schematic configuration of the receiving apparatus according to the fourth embodiment of the present invention.

As shown in FIG. 10, the antenna unit 101*b* includes an antenna switching unit 111*b*, a demodulating unit 111*b*, a binarizing unit 112*b*, a synchronization detector 113*b*, a signal strength detecting unit 114*b*, and an antenna unit power 115. The antenna unit 101*b* connects a plurality of antennas 105, is input a switching signal S14, and selectively switches one antenna out of the plurality of antennas 105. The demodulating unit 111*b* demodulates a radio frequency signal received via the antenna switching unit 110*b* into a baseband signal. The binarizing unit 112*b* binarizes the baseband signal demodulated by the demodulating unit 111*b* and outputs a binarization signal S11. The synchronization detector 113*b* uses the baseband signal demodulated by the demodulating unit 111*b* to detect a synchronization signal made of a vertical synchronization signal and a horizontal synchronization signal, and outputs a synchronization detection signal S12. The signal strength detecting unit 114*b* detects a signal strength of the radio frequency signal that undergoes the antenna switching unit 110*b* and is received by the antenna 105 (that is, a received strength of a radio signal received by any one of the plurality of antennas 105), and outputs an antenna strength signal S13 that corresponds to the detected signal strength. The antenna unit power 115 receives power supply from the receiving apparatus main body 101*a* by an electric signal S15 so that power is output to each functional unit within the antenna unit 101*b*.

The receiving apparatus main body 101*a* includes a signal processing unit 111*a*, an A/D converter 112*a*, a control unit 110*a*, a display unit 113*a*, a storage unit 114*a*, and a power of receiving apparatus main body 115*a*. The signal processing unit 111*a* is input the binarization signal S11 and the synchronization detection signal S12, and performs a process of obtaining an image signal. The A/D converter 112*a* is input the antenna strength signal S13, which is an analog signal, and converts it into a digital signal. The control unit 110*a* is input the image signal obtained by the signal processing unit 111*a*, and acquires the image data. The display unit 113*a* is connected to the control unit 110*a*, and simply displays the image data. The storage unit 114*a* is connected to the control unit 110*a*, and stores the image data. The power of receiving apparatus main body 115*a* supplies power to each functional unit within the receiving apparatus main body 101*a*, and supplies power to the antenna unit 101*b*. The control unit 110*a* an antenna selector 150 that outputs the switching signal S14 based on the digital signal output from the A/D converter 112*a*, and performs a switching control of the antenna switching unit 110*b*.

The antenna selector 150 controls the switching operation of the plurality of antennas 105 by the antenna switching unit 110*b* based on the signal strength of the radio frequency signal detected by the signal strength detecting unit 114*b*, that is, the receiving strength of the radio signal received via any one of the plurality of antennas 105. The antenna selector 150 selects an antenna of which receiving strength is the strongest (that is, an antenna suitable for receiving the radio signal) out of the plurality of antennas 105. In this case, the antenna selector 150 outputs the switching signal S14 for performing drive control of the antenna switching unit 110*b* so as to switch to the antenna selected in this manner.

The connector 101*c* detachably connects the antenna unit 101*b* and the receiving apparatus main body 101*a*, and forms a signal transmission path between the antenna unit 101*b* and the receiving apparatus main body 101*a*. More specifically, the connector 101*c* physically couples the antenna unit 101*b* and the receiving apparatus main body 101*a*, and electrically connects the antenna unit 101*b* and the receiving apparatus main body 101*a* so that the binarizing signal S11, the synchronization detection signal S12, the antenna strength signal S13, the switching signal S14, and an electric signal S15 are transmitted. In this case, the signals transmitted by the connector 101*c* are low-frequency signals, so that a low-frequency connector is used for the connector 101*c*. Accordingly, noise hardly occurs in the connector 101*c*. Therefore, the receiving apparatus main body 101*a* can be input the binarizing signal S11, the synchronization detection signal S12, and the antenna strength signal S13 that contains only an insignificant amount of noise. As a result, good image data that contains only an insignificant amount of noise can be acquired. A multi-pin connector can be used for the connector 101*c*, and the use of the multi-pin connector simplifies the fixation of the antenna unit 101*b* and the receiving apparatus main body 101*a*. The configuration of the low-frequency connector 101*c* is simpler than that of the radio frequency signal connector. The simple configuration has advantages in that the condition of the connector is not easily deteriorated even when the attaching and detaching are repeated, and the connector is thus imparted a long operating life.

In the fourth embodiment, in the receiving apparatus 101 the antenna unit 101b that demodulates the signal and the receiving apparatus main body 101a that acquires the image data are separated, and the both units are detachably coupled by the low-frequency connector 101c. Thus, this type of coupling prevents deterioration of the condition of the connector, which is caused due to repeated attaching and detaching of the antenna unit and the receiving apparatus main body, and noise can not easily enter from the connector 101c, whereby the receiving apparatus main body 101a can acquire good image data that contains only an insignificant amount of noise.

Fifth Embodiment

A fifth embodiment of the present invention is explained next. In the fourth embodiment, the antenna unit 101b and the receiving apparatus main body 101a are separated, and the signal is transmitted by the low-frequency connector 101c. In the fifth embodiment, the signal is transmitted by a photocoupler, and the antenna unit and the receiving apparatus main body are each provided with individual batteries.

Figure 11:
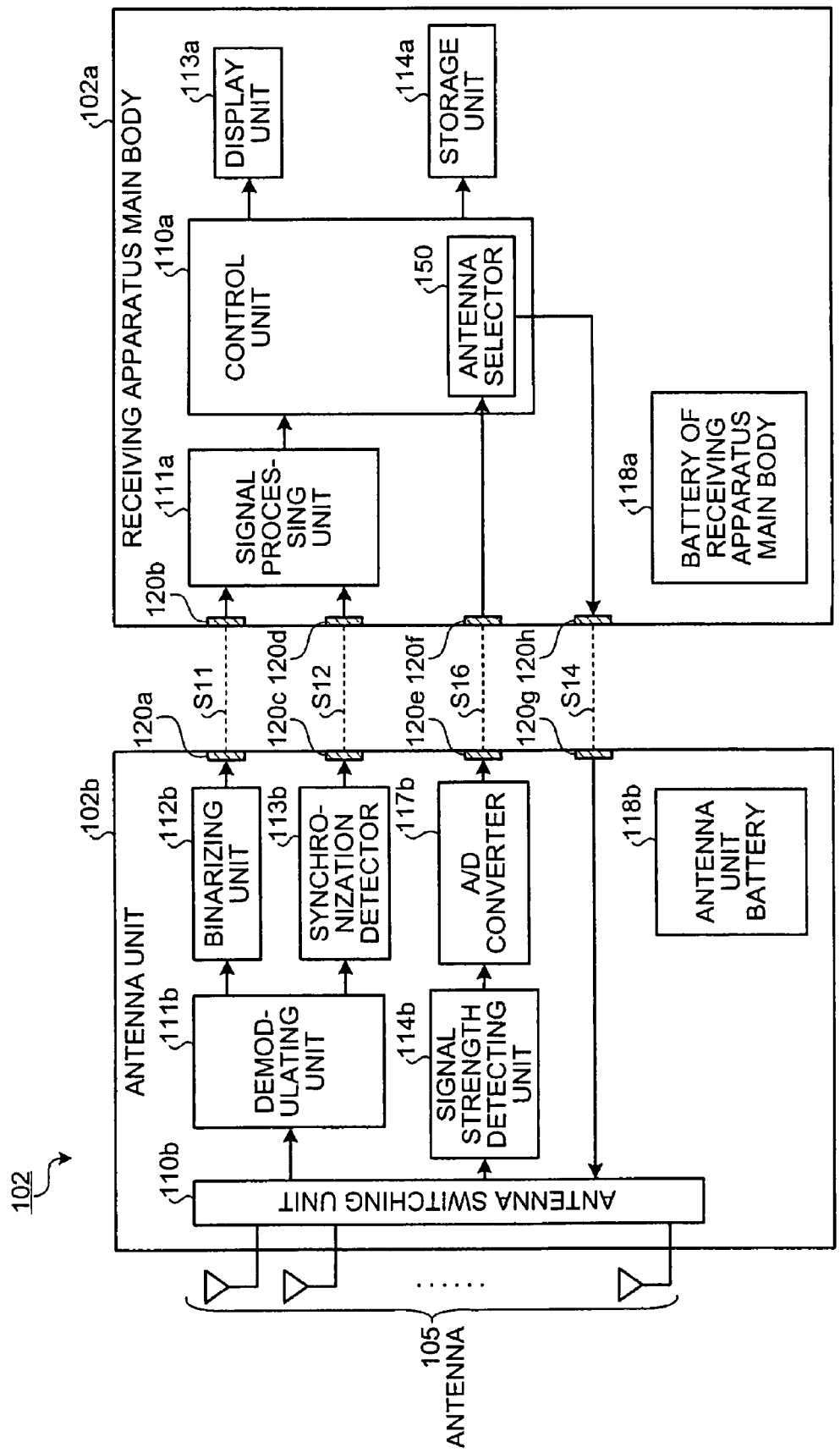
FIG. 11 is a block diagram showing a schematic configuration of a receiving apparatus according to a fifth embodiment of the present invention.

FIG. 11 is a block diagram showing a schematic configuration of a receiving apparatus 102 according to the fifth embodiment. As shown in FIG. 11, the receiving apparatus 102 includes an antenna unit 102b and a receiving apparatus main body 102. These units replace the antenna unit 101b and the receiving apparatus main body 101a of the above receiving apparatus 101 according to the fourth embodiment. In the antenna unit 102b, there are arranged an A/D converter 117b after a signal strength detecting unit 114b. The antenna unit 102b further includes light-emitting diodes 120a, 120c, and 120e; and a photodiode 120g. In the receiving apparatus main body 102a, there are arranged a light-emitting diode 120h, and photodiodes 120b, 120d, and 120f. The antenna unit 102b includes an antenna unit battery 118b that drives each functional unit of the antenna unit 102b. The antenna unit battery 118b replaces the above antenna unit power 115b. The receiving apparatus main body 102a includes a battery of receiving apparatus main body 118a that drives each functional unit of the receiving apparatus main body 102a. The battery of receiving apparatus main body 118a is used instead of the power of receiving apparatus main body 115a described above. Other configurations are the same as those of the fourth embodiment, and like parts are designated by like reference letters or numerals.

The light-emitting diodes 120a, 120c, 120e, and 120h correspond to the photodiodes 120b, 120d, 120f, and 120g to form the photocoupler. Such a photocoupler uses light as a medium for transmitting a signal between the antenna unit 102b and the receiving apparatus main body 102a. Thus, the photocoupler functions as means for transmitting the light between the antenna unit 102b and the receiving apparatus main body 102. The photocoupler blocks an electrical connection between the antenna unit 102b and the receiving apparatus main body 102 but provides insulation therebetween.

In the receiving apparatus 102, a binarization signal S11 output from a binarizing unit 112b is transmitted to a signal processing unit 111a by the photocoupler formed by the light-emitting diode 120a and the photodiode 120b. A synchronization detection signal S12 output from a synchronization detector 113b is transmitted to the signal processing unit 111a by the photocoupler formed by the light-emitting diode 120c and the photodiode 120d. The A/D converter 117b converts a detection signal (an antenna strength signal) detected by the signal strength detecting unit 114b into a digital signal S16. The digital signal S16 is transmitted to a control unit 110a by the photocoupler formed by the light-emitting diode 120e and the photodiode 120f. A switching signal S14 output from an antenna selector 150 within the control unit 110a is transmitted to an antenna switching unit 110b by the photocoupler formed by the light-emitting diode 120h and the photodiode 120g.

Between the antenna unit 102b and the receiving apparatus main body 102a, there is further provided a connecting unit (not shown) that detachably connects the casings of the both units, for example. In this case, the antenna unit 102b and the receiving apparatus main body 102a are connected by the connecting unit so that the light-emitting diodes 120a, 120c, 120e, and 120h correspond to the photodiodes 120b, 120d, 120f, and 120g, respectively, thereby forming the photocoupler. The antenna unit 102b and the receiving apparatus main body 102a are each provided with batteries (more specifically, the antenna unit battery 118b and the battery of receiving apparatus main body 118a) that drive each functional unit.

In the fifth embodiment, in the antenna unit 102b and the receiving apparatus main body 102a, there are provided the light-emitting diodes 120a, 120c, 120e, and 120h; and the photodiodes 120b, 120d, 120f, and 120g so that the photocouplers are formed. The antenna unit 101b and the receiving apparatus main body 101a are each provided with batteries. Therefore, the castings of the antenna unit 102b and the receiving apparatus main body 102a can be physically connected in a detachable manner, and do not have an electric junction, whereby high insulation can be retained while a communication connection is established therebetween. The receiving apparatus main body 102a can acquire good image data that contains only an insignificant amount of noise.

In the fifth embodiment, the receiving apparatus 102 does not include a connector that connects the antenna unit 101b and the receiving apparatus main body 101a. Therefore, advantageously, the absence of the connector does not obviously lead to the deterioration of the condition of the connector, which is caused due to repeated attaching and detaching of the antenna unit and the receiving apparatus main body; there is no need to apply a water-prevention treatment to the connector when the subject 1 is rinsed in alcohol; and the receiving apparatus 102 becomes convenient to use.

In the fifth embodiment, although the antenna unit 102b includes the A/D converter 117b so that the digital signal S16 that contains only an insignificant amount of noise is transmitted to the receiving apparatus main body 102a, the A/D converter 117b can be provided on the receiving apparatus main body 102a side. That is, the communication connection can be established by an analog baseband signal instead of the digital binarization signal S11.

The antenna unit battery 118b and the battery of receiving apparatus main body 118a explained in the fifth embodiment can be either a primary battery or a secondary battery.

Sixth Embodiment

A sixth embodiment of the present invention is explained next. In the sixth embodiment, when the antenna unit is attached to the receiving apparatus main body, a transformer is used to supply power to the antenna unit side from the receiving apparatus main body side.

Figure 12:
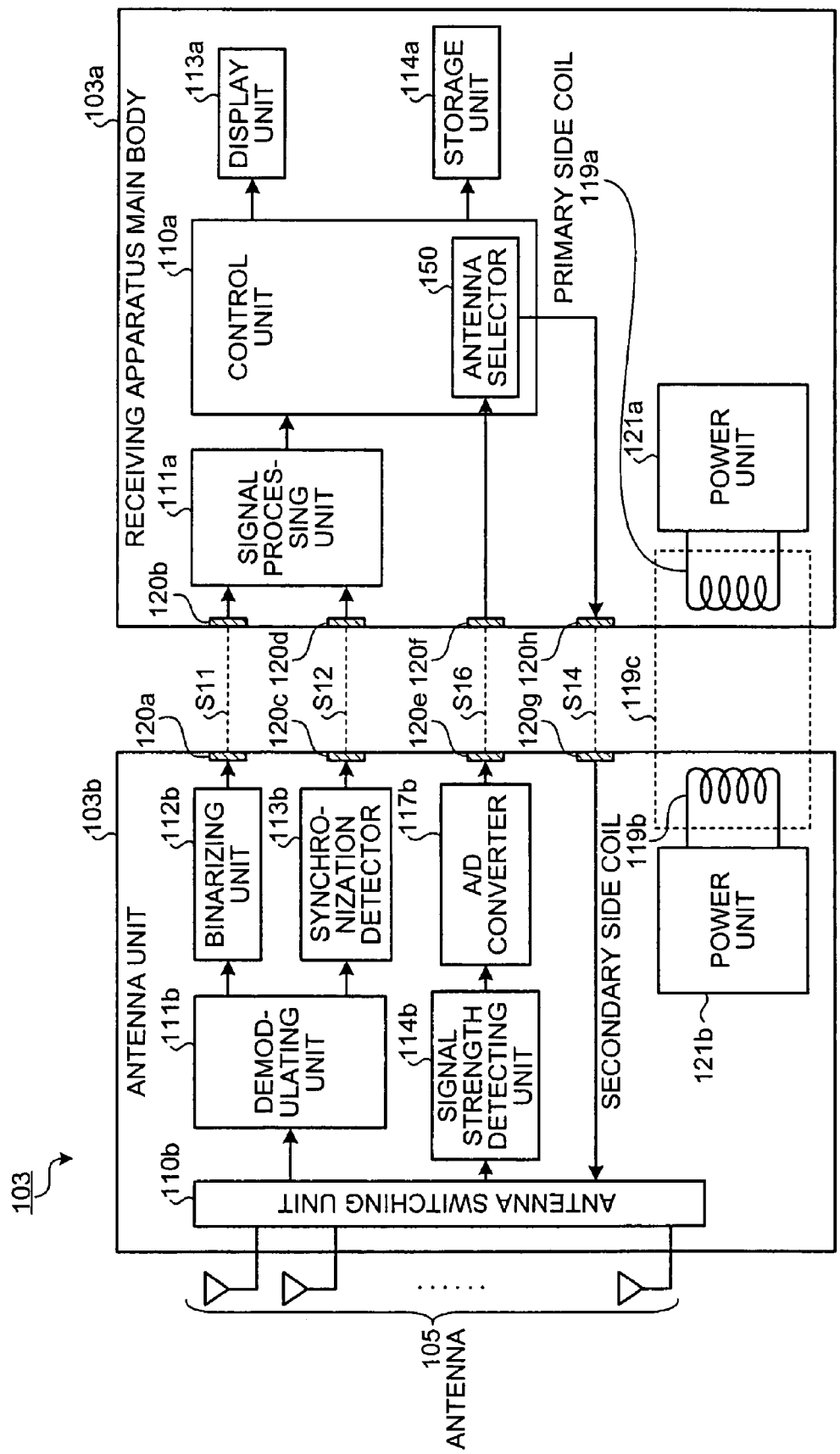
FIG. 12 is a block diagram showing a schematic configuration of a receiving apparatus according to a sixth embodiment of the present invention.

FIG. 12 is a block diagram showing a schematic configuration of a receiving apparatus 103 according to the sixth embodiment. As shown in FIG. 12, the receiving apparatus 103 includes an antenna unit 103b and a receiving apparatus main body 103a. These units replace the antenna unit 102b and the receiving apparatus main body 102a of the above receiving apparatus 102 according to the fifth embodiment. The antenna unit 103b includes a secondary side coil 119b and a power unit 121b instead of the antenna unit battery 118b explained in the fifth embodiment. The receiving apparatus main body 103a includes a primary side coil 119a and a power unit 121a instead of the battery of receiving apparatus main body 118a. Other configurations are the same as those of the fifth embodiment, and like parts are designated by like reference letters or numerals.

The power unit 121a supplies power to the receiving apparatus main body 101a and applies an alternating current to the primary side coil 119a. When the antenna unit 103b is detachably attached to the receiving apparatus main body 103a, a transformer 119c is formed by the primary side coil 119a and the secondary side coil 119b, and alternating electromotive force is generated in the secondary side coil 119b. The power unit 121b rectifies the alternating electromotive force and supplies power to each functional unit within the antenna unit 103b so that each functional unit is driven.

In the sixth embodiment, the formation of the transformer 119c supplies the antenna unit 103b with the power from the receiving apparatus main body 103a. Thus, the antenna unit 103b can supply a drive power to each functional unit even when a battery such as a battery cell is not individually provided, and the above effects of the fifth embodiment can be embraced. Not only a signal system but also a power system is insulated, whereby the inclusion of noise is further prevented. As a result, the receiving apparatus main body 103 can acquire good image data that contains only an insignificant amount of noise.

Seventh Embodiment

A seventh embodiment according to the present invention is explained next in detail. In the seventh embodiment, the antenna unit detachably connected to the receiving apparatus main body is configured to include a history storage unit that stores various pieces of information on a usage history of the antenna unit.

Figure 13:
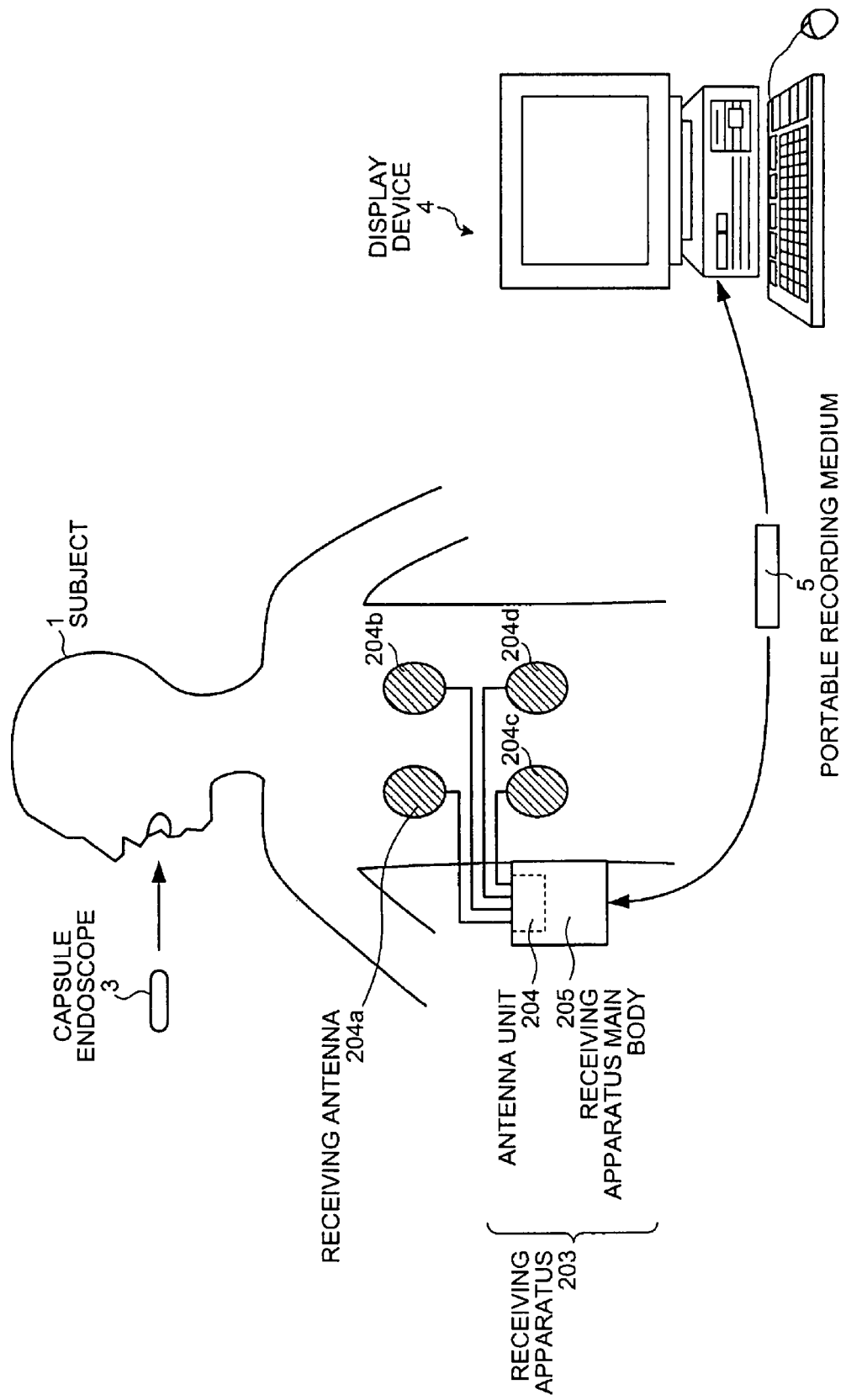
FIG. 13 is a schematic diagram schematically exemplifying one configuration example of a radio in-vivo information acquiring system using a receiving apparatus according to a seventh embodiment of the present invention.

The configuration of a radio in-vivo information acquiring system according to the seventh embodiment of the present invention includes an antenna unit and a receiving apparatus using the antenna unit is explained first. The configuration of the antenna unit and the receiving apparatus is explained next. FIG. 13 is a schematic diagram schematically exemplifying one configuration example of the radio in-vivo information acquiring system. As shown in FIG. 13, the radio in-vivo information acquiring system includes a capsule endoscope 3, a receiving apparatus 203, a display device 4, and a portable recording medium 5. The capsule endoscope 3 moves along a passing route in the interior of a subject 1 and images the interior of the subject 1. The receiving apparatus 203 receives image data imaged by the capsule endoscope 3. The display device 4 displays an image of the interior of the subject 1 based on the image data imaged by the capsule endoscope 3. The portable recording medium 5 exchanges information between the receiving apparatus 203 and the display device 4.

As explained above, the capsule endoscope 3 is provided with an imaging function of imaging the interior of the subject 1, and a radio communication function of transmitting the image data obtained by imaging inside the subject 1 to an external receiving apparatus (the receiving apparatus 203, for example). The capsule endoscope 3 sequentially images an image in the body cavity of the subject 1, and sequentially transmits the obtained image data inside the subject 1 to the receiving apparatus 203.

The display device 4 displays the image inside the subject 1 (body cavity image, for example) imaged by the capsule endoscope 3, as explained above. The portable recording medium 5 exchanges the data between the receiving apparatus and the display device 4 of the radio in-vivo information acquiring system according to the present invention, as explained above. In the seventh embodiment, the portable recording medium 5 is detachable to the receiving apparatus 203 and the display device 4, and is attached to the receiving apparatus 203 so as to sequentially store the data or the like transmitted from the capsule endoscope 3 while the capsule endoscope 3 moves in the body cavity of the subject 1. After the capsule endoscope 3 is discharged from the subject 1, the portable recording medium 5 is taken out from the receiving apparatus 203 and is attached to the display device 4. The stored image data or the like are read by the display device 4. Unlike a cable connection between the receiving apparatus 203 and the display device 4, the data exchange between the receiving apparatus 203 and the display device 4 by using the portable recording medium 5 provides the subject 1 with a free movement while the subject carries the receiving apparatus 203 even when the capsule endoscope 3 moves in the interior of the subject 1.

Although the portable recording medium 5 is used to exchange the data between the receiving apparatus main body 203 and the display device 4, the data exchange is not always limited thereto. Another built-in recording device, which is used as the receiving apparatus main body 203, and the display device 4 can be connected by wire or by radio to exchange the data between the both units.

To realize receiving antennas 204a to 204d, a loop antenna is employed, for example. The receiving antennas 204a to 204d receive a radio signal transmitted from the capsule endoscope 3. The receiving antennas 204a to 204d are each arranged at predetermined positions on the body surface of the subject 1, that is, positions that correspond to a passing route of the capsule endoscope 3, for example, as shown in FIG. 13. The receiving antennas 204a to 204d can be each arranged at predetermined positions on a jacket worn by the subject 1. In this case, when the subject 1 wears the jacket, the receiving antennas 204a to 204d each are to be arranged at the predetermined positions on the body surface of the subject 1. At least one receiving antenna is arranged on the subject 1. Preferably, a plurality of receiving antennas are arranged thereon. In this case, the number of receiving antennas to be arranged is not particularly limited to four.

The receiving apparatus 203 according to the seventh embodiment of the present invention performs a receiving process of a radio signal received via any one of the receiving antennas 204a to 204d. The receiving apparatus 203 includes an antenna unit 204 and a receiving apparatus main body 205 according to the seventh embodiment of the present invention. The antenna unit 204 is electrically connected to the receiving antennas 204a to 204d via cables. The antenna unit 204 transmits to the receiving apparatus main body 205 the image data or the like based on the radio signal received from the capsule endoscope 3 via any one of the receiving antennas 204a to 204d. The receiving apparatus main body 205 sequentially acquires the image data inside the subject 1 obtained by the capsule endoscope 3 via a predetermined radio wave transmitted and received between the capsule endoscope 3 and any one of the receiving antennas 204a to 204d. In this case, the plurality of receiving antennas are arranged on the subject 1 so as to correspond to the position of the capsule endoscope 3 inside the subject 1. Thereby, the receiving apparatus 203 can receive the image data obtained by the capsule endoscope 3 via a receiving antenna at the position suitable for receiving the radio signal.

Figure 14:
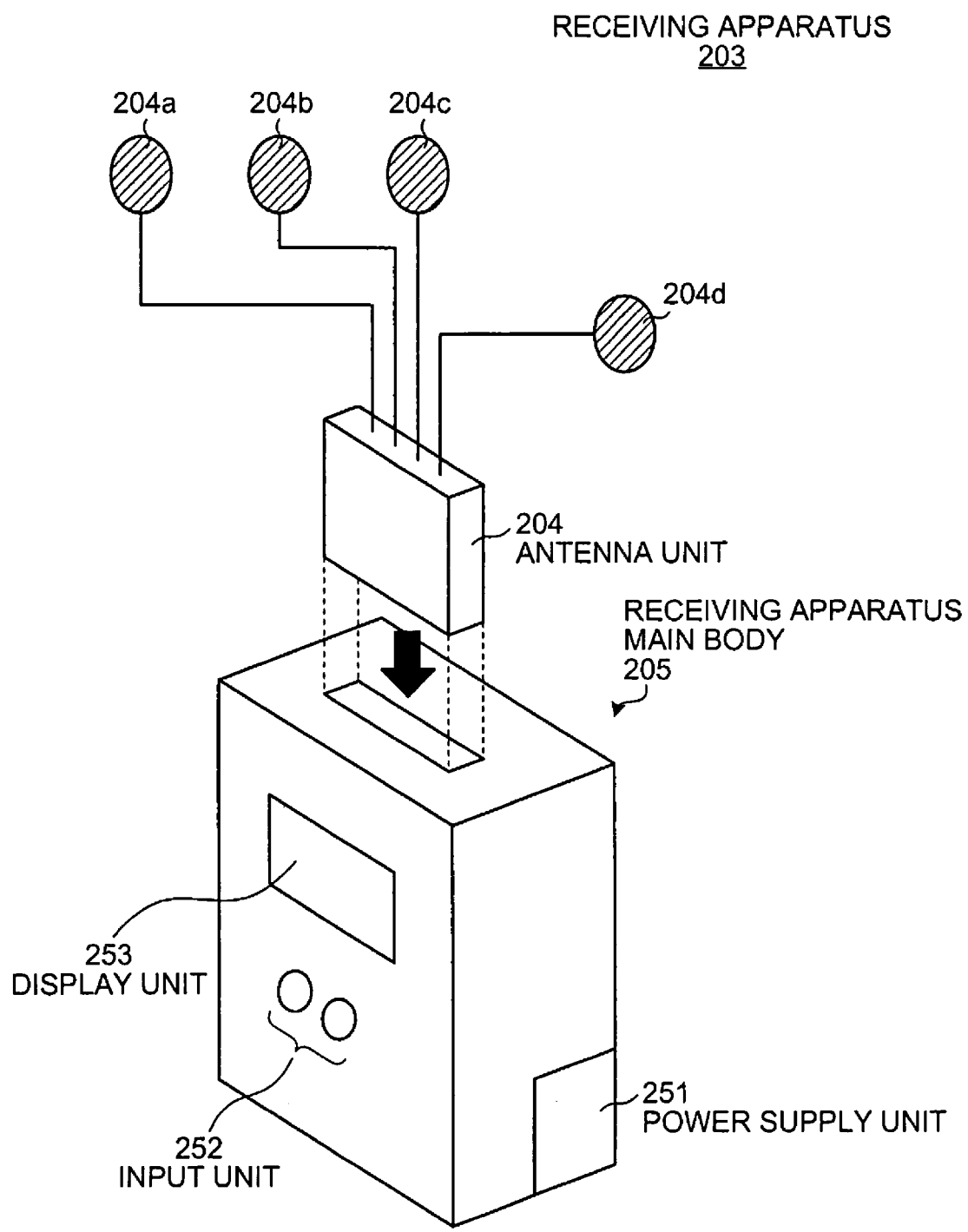
FIG. 14 is a schematic diagram schematically exemplifying a state in which the receiving apparatus is configured by an antenna unit and a receiving apparatus main body.

FIG. 14 is a schematic diagram schematically exemplifying a state in which the receiving apparatus 203 is configured by the antenna unit 204 and the receiving apparatus main body 205. As shown in FIG. 14, the antenna unit 204 retains the receiving antennas 204a to 204d via each cable, and is detachably attached to a predetermined portion of the receiving apparatus main body 205. In this case, the antenna unit 204 is electrically connected to the receiving apparatus main body 205 in a detachable manner via a connector, a terminal, and the like. To realize the receiving apparatus 203, the antenna unit 204 and the receiving apparatus main body 205 are thus electrically connected. The receiving apparatus main body 205 includes a power supply unit 251, an input unit 252, and a display unit 253. The power supply unit 251 supplies a drive power to each constituent unit of the receiving apparatus 203. The input unit 252 inputs instruction information for instructing the receiving apparatus 203. The display unit 253 displays and outputs the information.

Figure 15:
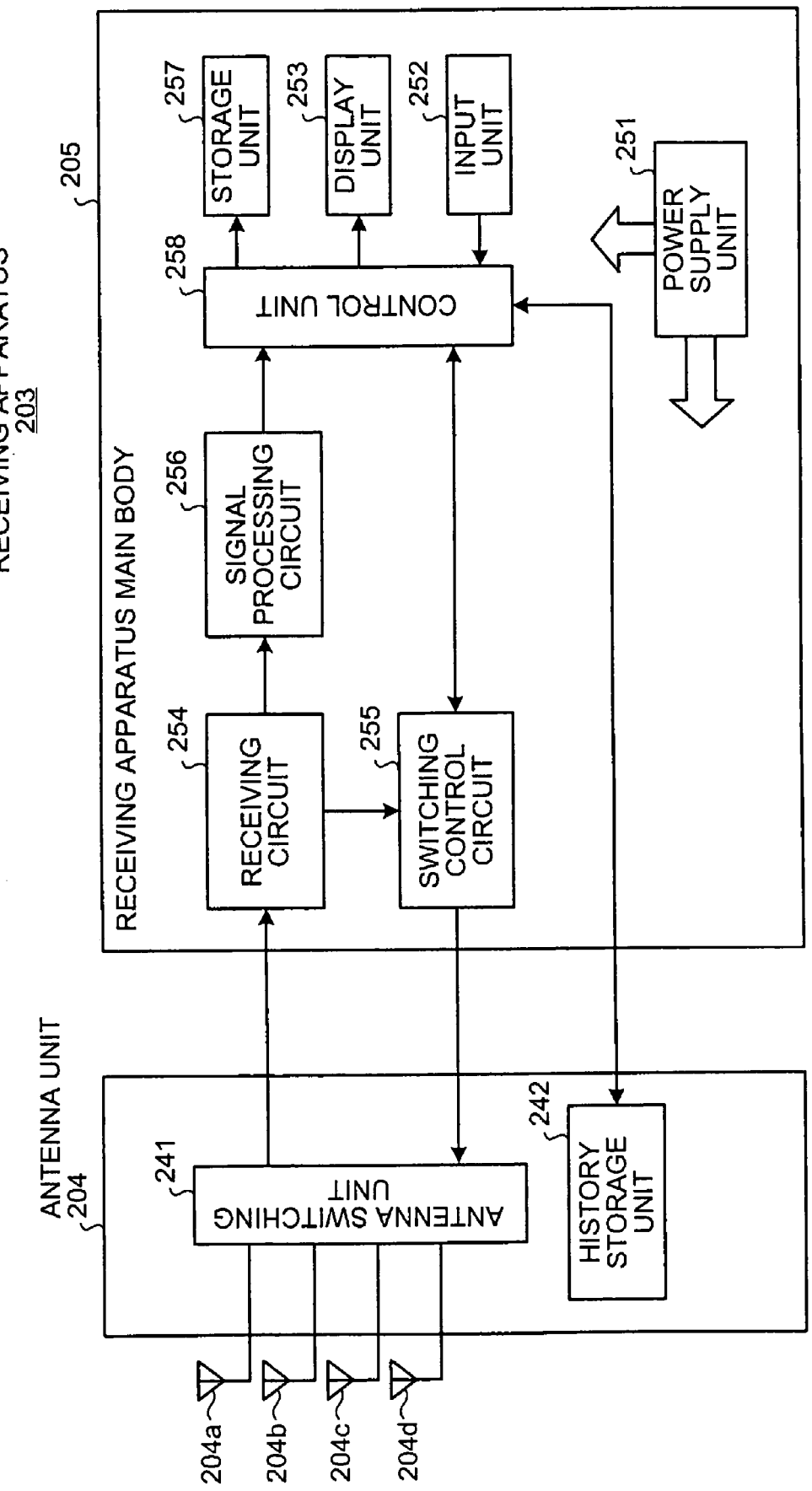
FIG. 15 is a block diagram schematically exemplifying one configuration example of an antenna unit according to a seventh embodiment of the present invention and a receiving apparatus using the antenna unit.

Next, the configuration of the receiving apparatus 203 is explained in detail. FIG. 15 is a block diagram schematically exemplifying one configuration example of the receiving apparatus 203. To realize the receiving apparatus 203, the antenna unit 204 and the receiving apparatus main body 205 are thus electrically connected, as explained above. As shown in FIG. 15, the antenna unit 204 includes an antenna switching unit 241 and a history storage unit 242. The antenna switching unit 241 selects a receiving antenna suitable for receiving a radio signal out of the receiving antennas 204a to 204d. The history storage unit 242 records information on a usage history of the antenna unit 204.

The antenna switching unit 241 performs an antenna switching operation for electrically connecting the receiving apparatus main body 205 with any one of the receiving antennas 204a to 204d retained by the antenna unit 204. The antenna switching unit 241 performs the antenna switching operation, and outputs to the receiving apparatus main body 205 the radio signal received via any one of the receiving antennas 204a to 204d.

To realize the history storage unit 242, a nonvolatile memory capable of rewriting information such as EEPROM or a flash memory or the like is employed, and the history storage unit 242 stores various pieces of information on the usage history as antenna history information. The antenna history information includes antenna times-of-use information, open-circuit detection information, open-circuit antenna information, detection-time times-of-use information, and normal state information. The antenna times-of-use information indicates the number of times that the antenna unit 204 is used. The open-circuit detection information indicates that any one of the retained receiving antennas 204a to 204d is in an open-circuit state. The open-circuit antenna information specifies a receiving antenna, out of the retained receiving antennas 204a to 204d, determined to be in the open-circuit state. The detection-time times-of-use information indicates the number of times that the antenna unit 204 is used when an open-circuit detecting process is performed on the retained receiving antennas. The normal state information indicates that all the retained receiving antennas are in a state capable of normally receiving the radio signal (normal state).

In contrast, as explained above, the receiving apparatus main body 205 includes the power supply unit 251 that supplies a drive power to each constituent unit of the receiving apparatus 203, the input unit 252 that inputs instruction information for instructing the receiving apparatus 203, and the display unit 253 that displays and outputs the information. The receiving apparatus main body 205 also includes a receiving circuit 254, a switching control circuit 255, and a signal processing circuit 256. The receiving circuit 254 applies a demodulation process, for example, on the radio signal received via any one of the receiving antennas 204a to 204d selected by the antenna switching unit 241, and detects a received electric-field strength (signal strength) of the radio signal. The switching control circuit 255 controls an antenna switching operation of the antenna switching unit 241 based on the received electric-field strength detected by the receiving circuit 254. The signal processing circuit 256 extracts the image data and the like obtained by the capsule endoscope 3, for example, based on the image signal extracted by the receiving circuit 254. The receiving apparatus main body 205 further includes a storage unit 257, and a control unit 258. The storage unit 257 stores information such as the image data. The control unit 258 performs drive control of each constituent unit of the receiving apparatus 203. The control includes control regarding a storing process, performed by the history storage unit 242, for the antenna history information; and control regarding a storage process, performed by the storage unit 257, for the image data and the like.

The power supply unit 251 supplies a drive power to each constituent unit of the receiving apparatus 203, as explained above. That is, the power supply unit 251 supplies the drive power to each constituent unit of the receiving apparatus main body 205, and supplies the drive power to each constituent unit of the antenna unit 204 electrically connected to the receiving apparatus main body 205. In this case, the power supply unit 251 supplies the drive power to each constituent unit of the receiving apparatus 203 even when the receiving apparatus 203 is carried by the subject 1 as shown in FIG. 13. Examples of the power supply unit 251 include a cell battery, a lithium-ion secondary battery, a nickel hydride battery. The power supply unit 251 can be rechargeable.

To realize the input unit 252, a plurality of input keys, a rotary switch, and the like are employed. The input unit 252 inputs to the control unit 258 the instruction information for instructing the receiving apparatus 203, that is, instruction information for instructing to switch an operation mode of the control unit 258 to an image receiving mode or to an open-circuit detecting mode, for example. More specifically, in response to an input operation of the user, the input unit 252 inputs to the control unit 258 image receiving mode instruction information for instructing to switch the operation mode to the image receiving mode, or open-circuit detecting mode instruction information for instructing to switch the operation mode to the open-circuit detecting mode. The image receiving mode is an operation mode in which a series of operations are performed. For example, in this case, the receiving apparatus 203 performs a series of operations ranging from receiving the image data imaged by the capsule endoscope 3 to acquiring the image data. On the other hand, the open-circuit detecting mode is an operation mode in which an open-circuit detecting process is performed on the receiving antennas 204a to 204d retained by the antenna unit 204.

To realize the display unit 253, a thin display such as a liquid crystal display or an organic EL display is employed. The display unit 253 displays the information based on the control of the control unit 258. The display unit 253 displays and outputs warning information on the antenna history information or information on the results of the open-circuit detecting process, for example.

The receiving circuit 254 performs a demodulation process or the like on a radio signal input from the antenna switching unit 241 and detects a received electric-field strength of the radio signal. More specifically, when receiving the radio signal from the capsule endoscope 3 via the antenna switching unit 241 and any one of the receiving antennas 204a to 204d, the receiving circuit 254 performs a demodulation process or the like for demodulating and extracting the image signal included in the radio signal. The receiving circuit 254 outputs the obtained image signal to the signal processing circuit 256. The receiving circuit 254 detects the received electric-field strength of the radio signal, and outputs to the switching control circuit 255 a strength detection signal (antenna strength signal) indicating the detected received-electric-field strength.

The switching control circuit 255 controls the above antenna switching operation performed by the antenna switching unit 241. More specifically, the switching control circuit 255 determines the receiving antenna suitable for receiving the radio signal out of the receiving antennas 204a to 204d based on the strength detection signal input from the receiving circuit 254, and controls the antenna switching unit 241 such that the determined receiving antenna and the receiving circuit 254 are electrically connected. When the control unit 258 sets the open-circuit detecting mode as the operation mode, the switching control circuit 255 is driven and controlled by the control unit 258, and outputs the strength detection signal to the control unit 258.

The signal processing circuit 256 extracts the image data and the like included in the image signal. The image signal is extracted by the receiving circuit 254. For example, when the image signal extracted by the receiving circuit 254 is an image signal generated by the capsule endoscope 3, the signal processing circuit 256 extracts the image data and the like imaged by the capsule endoscope 3 based on the image signal input from the receiving circuit 254. The signal processing circuit 256 outputs the obtained image data and the like to the control unit 258.

The storage unit 257 can be detachably attached to the above portable recording medium 5. The storage unit 257 sequentially writes into the portable recording medium 5 information based on the control of the control unit 258. The information includes the image data extracted by the signal processing circuit 256, for example. The storage unit 257 can be configured to include a RAM or a memory IC such as a flash memory so that the storage unit 257 itself stores the information.

To realize the control unit 258, a CPU (Central Processing Unit) that executes various processing programs, a ROM in which the various processing programs are recorded beforehand, and an EEPROM in which operation parameters for various processes, or various pieces of information such as antenna history information and the like are stored are employed. The control unit 258 controls drive of each constituent unit of the receiving apparatus main body 205, and controls drive of each constituent unit of the antenna unit 204 electrically connected to the receiving apparatus main body 205. In this case, the control unit 258 always monitors whether the above image receiving mode instruction information or the open-circuit detecting mode instruction information is input from the input unit 252. When such instruction information is input, the control unit 258 sets the operation mode according to the input instruction information, and performs drive control on each constituent unit of the receiving apparatus 203 based on the set operation mode.

Figure 16:
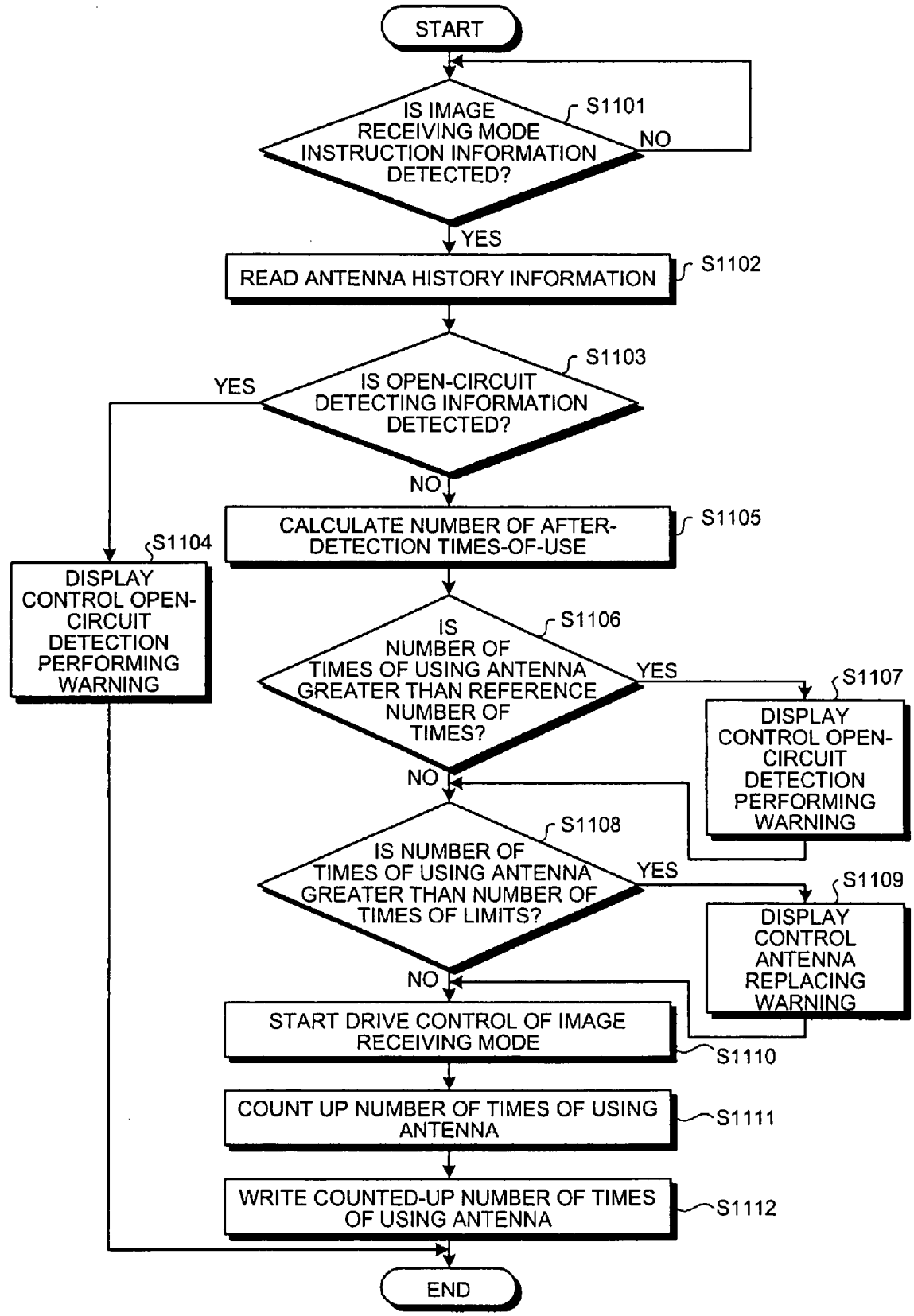
FIG. 16 is a flowchart for exemplifying a process procedure for starting drive control of an image receiving mode based on checking results of antenna history information.

For example, in the image receiving mode, the control unit 258 checks the number of times that the antenna unit 204 is used or the usage history of the retained receiving antenna such as an occurrence of an antenna open-circuit, based on the antenna history information stored in the history storage unit 242. The checking is performed before a start of the drive control of the image receiving mode. The control unit 258 displays on and outputs to the display unit a warning display corresponding to the checked results. Alternatively, based on the checked results, the control unit 258 starts the drive control of the image receiving mode on each constituent unit of the receiving apparatus 203. FIG. 16 is a flowchart for exemplifying a process procedure for controlling the warning display or for starting the drive control of the image receiving mode, based on the results obtained by checking the antenna history information.

In FIG. 16, unless the control unit 258 is input the image receiving mode instruction information from the input unit 252, the control unit 258 does not detect the image receiving mode instruction information (step S1101, No). The control unit 258 repeats the step S1101 until the image receiving mode instruction information is input from the input unit 252. That is, the control unit 258 always monitors whether the image receiving mode instruction information is input from the input unit 252.

On the other hand, when the control unit 258 is input the image receiving mode instruction information from the input unit 252, the control unit 258 detects the input image receiving mode instruction information (step S1101, Yes). The control unit 258 sets the image receiving mode as the operation mode, based on the detected image receiving mode instruction information. In the image receiving mode, the control unit 258 firstly reads the antenna history information recorded in the history storage unit 242 (step S1102). In this case, the control unit 258 checks a content of the antenna history information read from the history storage unit 242.

Next, when the control unit 258 detects the open-circuit detecting information based on the antenna history information after checking the antenna history information read in the step S1102 (step S1103, Yes), the control unit 258 determines that at least one of the receiving antennas 204a to 204d is open-circuit based on the open-circuit detecting information, and controls the display unit 253 such that an open-circuit detecting warning for warning the open-circuit to outside is displayed (step S1104). In this case, the control unit 258 can control the display unit 253 such that the open-circuit antenna information together with this open-circuit detecting warning are displayed on the display unit 253. Thereafter, the control unit 258 ends the process procedure without starting the drive control of the image receiving mode.

In contrast, when the control unit 258 does not detect the open-circuit detecting information based on the antenna history information after checking the antenna history information read in the step S1102 (step S1103, No), the control unit 258 extracts the antenna times-of-use information and the detection-time times-of-use information based on the antenna history information, and uses the extracted antenna times-of-use information and the detection-time times-of-use information to calculate the number of after-detection times-of-use of the antenna unit 204 (step S1105). The after-detection times-of-use indicates the number of times that the antenna unit 204 is used during a time that the last open-circuit detecting process is carried out on the antenna unit 204 and up to now, for example. Therefore, the control unit 258 can acquire the after-detection times-of-use by calculating the difference between the number of times that the antenna unit 204 is used based on the antenna times-of-use information and the number of times that the antenna unit 204 is used based on the detection-time times-of-use information. When the control unit 258 cannot extract the detection-time times-of-use information based on the antenna history information, the control unit 258 uses the number of times of use based on the extracted antenna times-of-use information as the after-detection times-of-use.

The control unit 258 then compares the number of the after-detection times-of-use calculated in the step S1105 and the reference number of times recorded beforehand as the determination reference information. When the after-detection times-of-use is greater than the reference number of times (step S1106, Yes), the control unit 258 controls the display unit 253 such that an open-circuit detection performing warning for prompting to perform an open-circuit detecting process on the antenna unit 204 is displayed (step S1107). The reference number of times is determination reference information for adjusting the performing frequency of the open-circuit detecting process. When the control unit 258 uses the reference number of times of which value is set to as small as possible, the control unit 258 can control the display unit 253 such that the open-circuit detection performing warning is frequently displayed and output.

After the process procedure in the step S1107 is completed, the control unit 258 compares the number of times of using the antenna based on the antenna history information and the number of times of limits recorded beforehand as the determination reference information. When the number of times of using the antenna is greater than the number of times of limits (step S1108, Yes), the control unit 258 controls the display unit 253 such that an antenna replacing warning for prompting a replacement of the antenna unit 204 by another antenna unit is displayed (step S1109). The number of times of limits is determination reference information for indicating a desired limit value of the number of times of use with which the antenna unit 204 can maintain the above normal state. When the control unit 258 uses the number of times of limits of which value is set to as small as possible, the control unit 258 can control the display unit 253 such that the antenna replacing warning is displayed and output early.

Thereafter, the control unit 258 starts the drive control of the image receiving mode on each constituent unit of the receiving apparatus 203 (step S1110), sequentially acquires the image data and the like imaged by the capsule endoscope 3, for example, and sequentially transfers the acquired image data and the like to the storage unit 257. Thereby, the storage unit 257 sequentially writes the image data and the like transferred from the control unit 258 into the portable recording medium 5, for example.

In response to the start of the drive control of the image receiving mode, which serves as a trigger, the control unit 258 counts up the number of times of using the antenna based on the antenna history information read in the above step S1102 (step S1111). The control unit 258 increases the number of times of using the antenna by 1. Thereafter, the control unit 258 writes into the history storage unit 242 the antenna times-of-use information for indicating the counted-up number of times of using the antenna (step S1112). In this case, the history storage unit 242 is input the counted-up number of times of using the antenna from the control unit 258. This number of times of using the antenna is overwritten on the number of times of using the antenna stored last time. Thereby, the number of times of using the antenna within the history storage unit 242 is updated.

The control unit 258 compares the number of the after-detection times-of-use calculated in the above step S1105 and the reference number of times. When the after-detection times-of-use is less than the reference number of times (step S1106, No), the control unit 258 compares and the number of times of limits and the number of times of using the antenna based on the above antenna history information read in the step S1102, without performing the above process procedure of the step S1107. When the number of times of using the antenna is less than the number of times of limits (step S1108, No) as a result of the comparison between the number of times of using the antenna and the number of times of limits, the control unit 258 performs the above process procedures from the step S1110 and onward, without performing the above process procedure of the step S1109.

The user visually recognizes the open-circuit detection warning displayed and output on the display unit 253 based on the above process procedure of the step S1104 so that the user can easily comprehend that the antenna unit 204 cannot normally receive the radio signal. The user also visually recognizes the open-circuit antenna information displayed and output on the display unit 253 so that the user can easily comprehend that any one of the receiving antennas 204a to 204d is in an open-circuit state. When such information is displayed, the user can electrically connect the normally working antenna unit and the receiving apparatus main body 205 instead of using the antenna unit 204 indicated by the open-circuit detection warning. Alternatively, the user can electrically connect the normally working receiving antenna and the antenna unit 204 instead of using the receiving antenna indicated by the open-circuit antenna information.

The user visually recognizes the open-circuit detection performing warning displayed and output on the display unit 253 based on the above process procedure in the step S1107 so that the user can easily comprehend that the open-circuit detecting process on the antenna unit 204 is not performed for a predetermined period. The user simply needs to perform the open-circuit detecting process on the antenna unit 204 at every time the open-circuit detection performing warning is displayed and output on the display unit 253.

The user visually recognizes the antenna replacing warning displayed and output on the display unit 253 based on the above process procedure in the step S1109 so that the user can easily comprehend that the number of times that the antenna unit 204 is used is greater than the desired number of times of limits. In this case, the user simply needs to replace the antenna unit electrically connected to the receiving apparatus main body 205 by another normally operating antenna unit at every time the antenna replacing warning is displayed and output on the display unit 253. Thereby, the user can replace the antenna unit by the normally operating antenna unit before any one of the receiving antennas retained by the antenna unit is open-circuit. The user can always use the receiving apparatus 203 provided with the antenna unit in the normal state and the receiving apparatus main body 205.

On the other hand, in the above open-circuit detecting mode, the control unit 258 determines each receiving state of the radio signal received by the receiving antennas 204a to 204d, for example, so as to perform the open-circuit detecting process on the antenna unit 204. In this case, the user arranges a radio signal generating device (not shown) that generates and outputs a test radio signal of the same frequency band as the radio signal transmitted by the capsule endoscope 3 near the receiving antennas 204a to 204d subject to an open-circuit detection. The receiving antennas 204a to 204d are made to receive the test radio signal from the radio signal generating device. The control unit 258 performs the open-circuit detecting process on the antenna unit 204, based on a received electric-field strength of the test radio signal received via the receiving antennas 204a to 204d.

Figure 17:
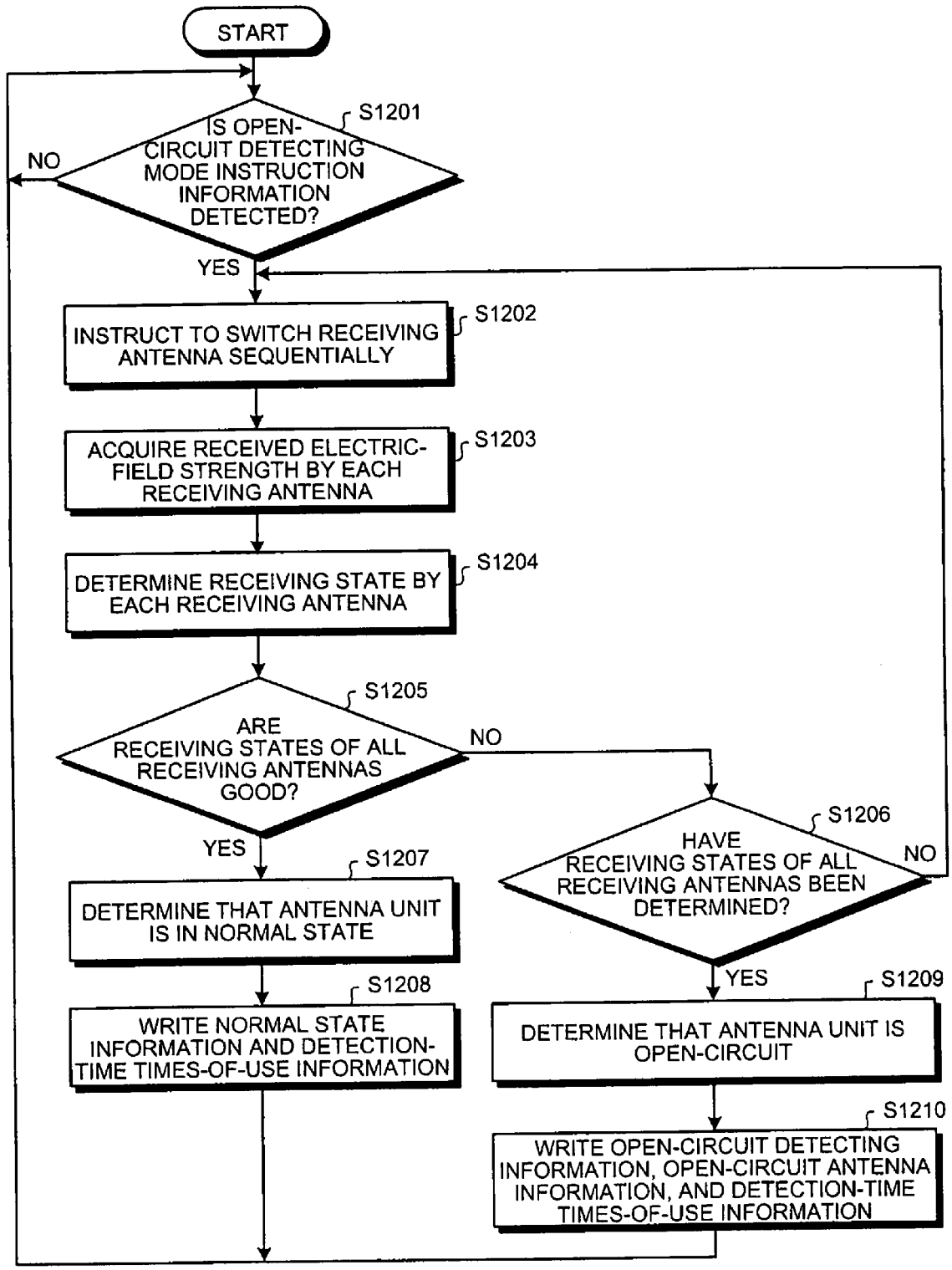
FIG. 17 is a flowchart for exemplifying a process procedure of an open-circuit detection process in an open-circuit detecting mode.

FIG. 17 is a flowchart for exemplifying a process procedure of the open-circuit detecting process performed by the control unit 258 in the open-circuit detecting mode. In FIG. 17, unless the control unit 258 is input the open-circuit detecting mode instruction information from the input unit 252, the control unit 258 does not detect the open-circuit detecting mode instruction information (step S1201, No). The control unit 258 repeats the step S1201 until the open-circuit detecting mode instruction information is input from the input unit 252. That is, the control unit 258 always monitors whether the open-circuit detecting mode instruction information is input from the input unit 252.

In contrast, when the open-circuit detecting mode instruction information is input from the input unit 252, the control unit 258 detects the input open-circuit detecting mode instruction information (step S1201, Yes). The control unit 258 sets the open-circuit detecting mode as the operation mode based on the detected open-circuit detecting mode instruction information. In the open-circuit detecting mode, the control unit 258 firstly instructs the switching control circuit 255 to sequentially switch in a predetermined order the receiving antenna to be electrically connected to the receiving circuit 254 out of the receiving antennas 204a to 204d (step S1202). In this case, the switching control circuit 255 controls the antenna switching operation of the antenna switching unit 241 based on the control of the control unit 258, and controls such that the receiving antenna to be electrically connected to the receiving circuit 254 is sequentially switched in the predetermined order.

In this state, the above radio signal generating device is already arranged near the receiving antennas 204a to 204d, and transmits the test radio signal to the receiving antenna 204a to 204d. The receiving circuit 254 detects a received electric-field strength of the test radio signal, by each receiving antenna, received via the sequentially switched receiving antennas 204a to 204d. The receiving circuit 254 sequentially outputs a strength detection signal that corresponds to each received electric-field strength to the switching control circuit 255. The switching control circuit 255 sequentially transfers to the control unit 258 the strength detection signal sequentially input from the receiving circuit 254. The control unit 258 receives the strength detection signal from the switching control circuit 255 by each receiving antenna. The control unit 258 acquires, by each receiving antenna, the received electric-field strength of the test radio signal received via each receiving antenna 204a to 204d based on each of the received strength detection signals (step S1203).

The control unit 258 uses the received electric-field strength of each receiving antenna acquired in the step S1203 and a threshold value recorded beforehand as the determination reference information so as to determine each receiving state of the receiving antennas 204a to 204d by each receiving antenna (step S1204). In this case, the control unit 258 performs a comparison process, by each receiving antenna, in which each of the acquired received electric-field strengths and the threshold value are compared. The control unit 258 determines that the receiving state of the receiving antenna in which the received electric-field strength greater than the threshold value is acquired is good. The control unit 258 determines that the receiving state of the other antennas is not good.

In a step S1204, the control unit 258 determines whether the receiving states of all the receiving antennas 204a to 204d, which are subject to the open-circuit detection, are good. Unless determined that the receiving states are good (step S1205, No), the control unit 258 checks whether the receiving states of all the receiving antennas 204a to 204d have been completed. In this case, unless the control unit 258 detects that a period has passed, that is, a period during which the antenna switching operation in which each of all the receiving antennas 204a to 204d subject to the open-circuit detection and the receiving circuit 254 are electrically connected is repeated for a predetermined number of times, the control unit 258 determines that the receiving states of some of the receiving antennas 204a to 204d are not determined (step S1206, No). The control unit 258 repeats the above process procedures from the step S1202 and onward. On the other hand, when the control unit 258 detects that the period has been passed, the control unit 258 determines that the determination of the receiving states of all the receiving antennas 204a to 204d is completed (step S1206, Yes). The control unit 258 determines a receiving antenna of which receiving state is not good, out of the receiving antennas 204a to 204d subject to the open-circuit detection, is open-circuit. The control unit 258 determines that the antenna unit 204 retaining these receiving antennas 204a to 204d is open-circuit (step S1209).

Thereafter, the control unit 258 outputs to the history storage unit 242 open-circuit detecting information, open-circuit antenna information, and detection-time times-of-use information. The open-circuit detecting information indicates that at least one of the receiving antennas 204a to 204d subject to the open-circuit detection is open-circuit, that is, the antenna unit 204 is open-circuit. The open-circuit antenna information specifies the receiving antenna of which receiving state is determined to be not good in the above step S1204, that is, the receiving antenna determined to be open-circuit. The detection-time times-of-use information indicates the number of times of using the antenna at the time that the open-circuit detecting process is performed. The control unit 258 writes into the history storage unit 242 the output open-circuit detecting information, the open-circuit antenna information, and the detection-time times-of-use information (step S1210). In this case, the history storage unit 242 stores the open-circuit detecting information and the open-circuit antenna information as the antenna history information on the antenna unit 204, and overwrites the detection-time times-of-use information. Thereafter, the control unit 258 repeats the above process procedures from the step S1201 and onward.

The open-circuit antenna information can be any information as long as it can specify the receiving antennas 204a to 204d. Examples of the open-circuit antenna information include a number, a symbol, and a character, which are allotted to each of the receiving antennas 204a to 204d, for example. The number, the symbol, and the character can be used singly or used in combination.

On the other hand, in the step S1204, the control unit 258 determines whether the receiving states of all the receiving antennas 204a to 204d subject to the open-circuit detection are good. When determining that the receiving states are good (step S1205, Yes), the control unit 258 determines that the antenna unit 204 retaining these receiving antennas 204a to 204d are in the normal state (step S1207). Thereafter, the control unit 258 outputs to the history storage unit 242 normal state information and detection-time times-of-use information. The normal state information indicates that all the receiving antennas 204a to 204d subject to the open-circuit detection are in a state capable of normally receiving the radio signal, that is, the antenna unit 204 is in a normal state. The detection-time times-of-use information indicates the number of times of using the antenna at the time that the open-circuit detecting process is performed. The control unit 258 writes into the history storage unit 242 the output normal state information and detection-time times-of-use information (step S1208). In this case, the history storage unit 242 stores the normal state information as the antenna history information on the antenna unit 204, and overwrites the detection-time times-of-use information. Thereafter, the control unit 258 repeats the above process procedures from the step S1201 and onward.

The control unit 258 can control the display unit 253 such that the normal state information is displayed and output after performing the above process procedure in the step S1208. Alternatively, the control unit 258 can also control the display unit 253 such that the open-circuit detecting information and the open-circuit antenna information are displayed and output after performing the above process procedure of the step S1210. Thereby, the user can check results of the open-circuit detection process of the antenna unit, subject to the open-circuit detection, in a real time manner.

The function of the above radio signal generating device is at least to transmit the test radio signal of the same frequency band as the radio signal transmitted by the capsule endoscope 3. The radio signal generating device preferably generates and outputs the test radio signal including the image signal of the same signal pattern as that of the capsule endoscope 3. Thereby, the control unit 258 can perform the open-circuit detecting process by using a more practical test radio signal. As a substitute for the radio signal generating device, a dummy capsule having, in the interior of a casing structure similar to that of the capsule endoscope, a function of generating and outputting the test signal can be used. The capsule endoscope itself can be used therefor.

Note that although in the seventh embodiment of the present invention, the antenna times-of-use information indicating the number of times that the antenna unit 204 is used is recorded in the history storage unit 242 as one of the pieces of the antenna history information, the present invention is not limited thereto. A usage time counter indicating a usage time of the antenna unit 204, in which a unit time value is a predetermined unit time "1", can be recorded in the history storage unit 242 instead of the number of times of using the antenna. In this case, in the above image receiving mode, the control unit 258 sequentially counts up the usage time counter at each time a predetermined unit time, 30 minutes, for example, passes from a start of the drive control of the image receiving mode, and controls such that the counted-up usage time counter is overwritten in the history storage unit 242. The control unit 258 can use the usage time counter and information on the time based thereon instead of the information on the number of times of using the antenna unit in each process procedure of the above steps S1101 to S1112.

In the seventh embodiment of the present invention, the number of times of using the antenna is counted up at every start of the drive control of the image receiving mode. However, the present invention is not limited thereto. The present invention can be configured such that in an initial condition of the antenna unit 204, the number of times of limits to use the antenna unit 204, or a limit time counter indicating a usage limit time by using the above unit time value is recorded in the history storage unit 242 beforehand, and the control unit 258 counts down the number of times of limits to use or the limit time counter at every start of the drive control of the image receiving mode. In this case, when the control unit 258 detects that the number of times of limits to use or the limit time counter reaches zero, the control unit 258 determines that the number of times of use or the usage time of the antenna unit 204 reaches its limit, and controls the display unit 253 such that the antenna replacing warning is displayed and output. Thereby, it becomes easy to set the number of times of limits to use or the usage limit time by each antenna unit, and eliminates the need of changing a setting on the receiving apparatus side, that is, the reference number of times mentioned above or the number of times of limits by each antenna unit. Thus, a process of checking the usage history by each antenna unit is simplified.

In the seventh embodiment of the present invention, the receiving state of the receiving antenna is determined based on the received electric-field strength of the radio signal received by the receiving antenna subject to the open-circuit detection. The present invention is not limited thereto. The receiving state of the receiving antenna can be determined to be good when the image data based on the radio signal received via the receiving antenna is detected. The receiving state of the receiving antenna can also be determined to be good when the synchronization of the radio signal received via the receiving antenna is detected.

In the seventh embodiment of the present invention, the receiving apparatus 203 is configured of the receiving apparatus main body 205, and the antenna unit 204 includes the antenna switching unit 241 and the history storage unit 242 to each of which the receiving antennas 204a to 204d are electrically connected. However, the configuration of the present invention is not limited thereto. The receiving apparatus can be configured of an antenna unit, and a receiving apparatus main body. The antenna unit includes the antenna switching unit 241 to which the receiving antennas 204a to 204d are electrically connected, the history storage unit 242, the receiving circuit 254, and the switching control circuit 255. The receiving apparatus main body includes the power supply unit 251, the input unit 252, the signal processing circuit 256, the storage unit 257, and the control unit 258.

In this case, such an antenna unit outputs an image signal extracted through the demodulation process performed by the receiving circuit 254 (that is, a baseband signal demodulated from the radio signal by the receiving circuit 254) to the signal processing circuit 256 of the receiving apparatus main body. The antenna unit and the receiving apparatus main body like this can be detachably connected, almost similar to any one of the cases of the first to third embodiments, by using a connector that transmits the baseband signal. The adoption of the configuration that combines the seventh embodiment and any one of the first to third embodiments can allow the receiving apparatus according to the seventh embodiment to further embrace the effects of the first to third embodiments.

In contrast, in the antenna unit and the receiving apparatus main body that configure such a receiving apparatus according to the seventh embodiment, the both units can be detachably connected by using a low-frequency signal connector, almost similar to the case of the fourth embodiment. Each casing of the both units is detachably connected, and the photocoupler is used to transmit a signal between the both units, almost similar to the cases of the fifth and sixth embodiments. The adoption of the configuration that combines the seventh embodiment and any one of the fourth to sixth embodiments can allow the receiving apparatus according to the seventh embodiment to further embrace the effects of the fourth to sixth embodiments.

As explained above, in the seventh embodiment of the present invention, there is provided the history storage unit that can record the antenna history information including various pieces of information on the usage history of the retained receiving antenna. Examples of such information include the number of times of use, the usage time, and presence or absence of the open-circuit. Thus, it is possible to realize the antenna unit capable of easily checking the usage history of the receiving antenna based on the antenna history information recorded in the history storage unit, and easily checking by each unit whether all the retained receiving antennas can normally receive the radio signal.

The receiving apparatus is configured such that the receiving apparatus main body and the antenna unit are electrically connected in a detachable manner. The receiving apparatus main body includes a function capable of acquiring the image data by a capsule endoscope based on the radio signal that undergoes the antenna unit and is received from the capsule endoscope; a function of checking the usage history of the antenna unit based on the antenna history information recorded in the history storage unit of the antenna unit and performing a warning display based on the checked usage history; and a function of sequentially updating the antenna history information corresponding to the usage history of the antenna unit. Therefore, it is possible to realize a receiving apparatus capable of easily checking visually the usage history of the antenna unit, in particular, whether all the receiving antennas electrically connected to the antenna unit can normally receive the radio signal, before performing a process of acquiring the image data by the capsule endoscope.

According to the receiving apparatus, it is possible to prevent starting of a process of acquiring the image data imaged by the capsule endoscope when the open-circuit receiving antenna is used. The user can perform the process of acquiring the image data by always using the receiving apparatus including the antenna unit capable of normally receiving the radio signal. Thereby, the receiving apparatus can surely accumulate the image data imaged by the capsule endoscope, and enhance the reliability of examinations performed on the subject.

Industrial Applicability

As explained above, the antenna unit according to the present invention and the receiving apparatus using the same are effective for detachably connecting a receiving apparatus main body and an antenna unit including a receiving antenna. The present invention is particularly suitable for receiving and accumulating image data imaged by the capsule endoscope.

The invention claimed is:

1. A receiving apparatus, comprising:
an antenna unit that is electrically connected in a detachable manner to a receiving apparatus main body, the antenna including:
at least one receiving antenna that performs a radio communication with the capsule endoscope, the antenna unit transmitting the image data received via any one of the at least one receiving antenna to the receiving apparatus main body; and
a storage unit that can store usage history information on a usage history of the receiving antenna in an updatable manner; and
the receiving apparatus main body that receives via the antenna unit image data imaged by a capsule endoscope inserted in an interior of a subject, and accumulates the received image data, the receiving apparatus main body including:
an input unit that receives an input of open-circuit detecting mode instruction information,
a controller that detects the open-circuit detecting mode instruction information when the input unit receives the open-circuit detecting mode instruction information, and sets an operation mode to an open circuit detecting mode based on the detected open-circuit detecting mode instruction information, and
a receiving unit that outputs a strength detection signal of each of the receiving antennas when the controller sets the open-circuit detecting mode as the operation mode.

2. The receiving apparatus according to claim 1, wherein the controller controls the storage unit such that the storage unit stores the usage history information.

3. The receiving apparatus according to claim 2, wherein the controller performs drive control of the receiving apparatus main body that receives the image data, and updates the times-of-use information in the storage unit at every start of the drive control of the receiving apparatus main body.

4. The receiving apparatus according to claim 2, wherein the controller performs drive control of the receiving apparatus main body that receives the image data, and updates the usage time information in the storage unit at every time a predetermined unit time passes from a start of the drive control of the receiving apparatus main body.

5. The receiving apparatus according to claim 2, wherein the controller reads the usage history information in the storage unit before a start of drive control of the receiving apparatus main body, and determines whether to start the drive control of the receiving apparatus main body based on a content of the read usage history information.

6. The receiving apparatus according to claim 2, wherein based on each of receiving results of one or more receiving antennas retained by the antenna unit, the controller performs an open-circuit detection process of detecting whether at least one of the one or more receiving antennas is open-circuit.

7. The receiving apparatus according to claim 6, wherein the controller controls the storage unit such that the storage unit stores information indicating a state of the open-circuit as the open-circuit occurrence information when the controller determines that at least one of the one or more receiving antennas is open-circuit.

8. The receiving apparatus according to claim 6, wherein the controller detects the number of times of using the receiving antenna at the time that the open-circuit detection process is performed based on the times-of-use information in the storage unit, and controls the storage unit such that the storage unit stores information indicating the detected number of times of use as the detection performing history information.

9. The receiving apparatus according to claim 2, comprising a displayer that displays warning information on the antenna unit, wherein the controller controls the displayer based on a content of the read usage history information such that the displayer displays the warning information.

10. The receiving apparatus according to claim 9, wherein the warning information is one of:
information for warning that at least one of the one or more receiving antennas retained by the antenna unit is open-circuit;
information for warning that it is necessary to perform an open-circuit detection process on the antenna unit; and
information for warning that it is necessary to replace the antenna unit.

11. The receiving apparatus according to claim 1, wherein the receiving apparatus main body further includes a displayer that displays an open-circuit detection performing warning for prompting to perform an open-circuit detecting process when a number of after-detection times-of-use is greater than a predetermined number.

12. The receiving apparatus according to claim 1, wherein the usage history information includes at least one of:
times-of-use information indicating the number of times of using the receiving antenna;
usage time information indicating a usage time of the receiving antenna;
open-circuit occurrence information indicating occurrence of an open-circuit of the receiving antenna; and
detection performing history information indicating a performing history of an open-circuit detection process on the receiving antenna.

13. The receiving apparatus according to claim 1, wherein the storage unit is a nonvolatile memory.

* * * * *